(12) United States Patent
Kokoris et al.

(10) Patent No.: US 8,586,301 B2
(45) Date of Patent: Nov. 19, 2013

(54) MULTIPLEXED IDENTIFICATION OF NUCLEIC ACID SEQUENCES

(75) Inventors: Mark Stamatios Kokoris, Bothell, WA (US); Robert N. McRuer, Mercer Island, WA (US)

(73) Assignee: Stratos Genomics, Inc., Seattle, WA (US)

( * ) Notice: Subject to any disclaimer, the term of this patent is extended or adjusted under 35 U.S.C. 154(b) by 236 days.

(21) Appl. No.: 13/174,054

(22) Filed: Jun. 30, 2011

(65) Prior Publication Data

US 2012/0071330 A1 Mar. 22, 2012

Related U.S. Application Data

(60) Provisional application No. 61/360,385, filed on Jun. 30, 2010.

(51) Int. Cl.
*C12Q 1/68* (2006.01)
*C07H 21/02* (2006.01)
*C07H 21/04* (2006.01)

(52) U.S. Cl.
USPC .......................... 435/6.1; 536/23.1; 536/24.3

(58) Field of Classification Search
USPC .................................. 435/6.1; 536/23.1, 24.3
See application file for complete search history.

(56) References Cited

U.S. PATENT DOCUMENTS

| 4,988,167 | A | * | 1/1991 | Fergason | 349/195 |
| 5,415,839 | A | * | 5/1995 | Zaun et al. | 422/64 |
| 6,267,872 | B1 | * | 7/2001 | Akeson et al. | 205/775 |
| 6,537,755 | B1 | | 3/2003 | Drmanac | |
| 7,939,259 | B2 | | 5/2011 | Kokoris et al. | 435/6 |
| 2004/0005585 | A1 | * | 1/2004 | Bi et al. | 435/6 |
| 2004/0110162 | A1 | | 6/2004 | Shuber et al. | |
| 2004/0248104 | A1 | | 12/2004 | Yakhini et al. | |
| 2007/0037152 | A1 | | 2/2007 | Drmanac | |
| 2010/0297644 | A1 | | 11/2010 | Kokoris et al. | 435/6 |
| 2011/0237787 | A1 | | 9/2011 | Kokoris et al. | 536/24.3 |
| 2011/0251079 | A1 | | 10/2011 | Kokoris et al. | 506/7 |

FOREIGN PATENT DOCUMENTS

| EP | 0 185 494 A2 | 6/1986 |
| EP | 1 251 136 A2 | 10/2002 |
| FR | 2 747 396 A1 | 10/1997 |
| WO | 2007/120265 A2 | 10/2007 |
| WO | 2008/157696 A2 | 12/2008 |
| WO | 2009/055617 A1 | 4/2009 |
| WO | 2010/088557 A1 | 8/2010 |
| WO | 2012/003330 A2 | 1/2012 |

OTHER PUBLICATIONS

Phillips et al., Evaluation of the Genplex SNP typing system and a 49plex forensic marker panel. Forensic Science International : Genetics 1 :180 (2007).*
Wiedmann et al., Ligase Chain Reaction (LCR)—Overview and Applications. PCR Methods and Applications 3 :551 (1994).*
Branton et al., "The potential and challenges of nanopore sequencing," *Nature Biotechnology* 26(10):1146-1153, Oct. 2008.
Derrington et al., "Nanopore DNA sequencing with MspA," *PNAS* 107(37):16060-16065, Sep. 14, 2010.

* cited by examiner

*Primary Examiner* — Ethan C Whisenant
(74) *Attorney, Agent, or Firm* — Seed IP Law Group PLLC

(57) ABSTRACT

A method for the rapid identification of a target nucleic acid sequence is provided, as well as corresponding devices, products and kits. Such methods are useful for the rapid detection, identification and/or quantification of target nucleic acid sequences associated with, for example, a pathogen.

31 Claims, 19 Drawing Sheets

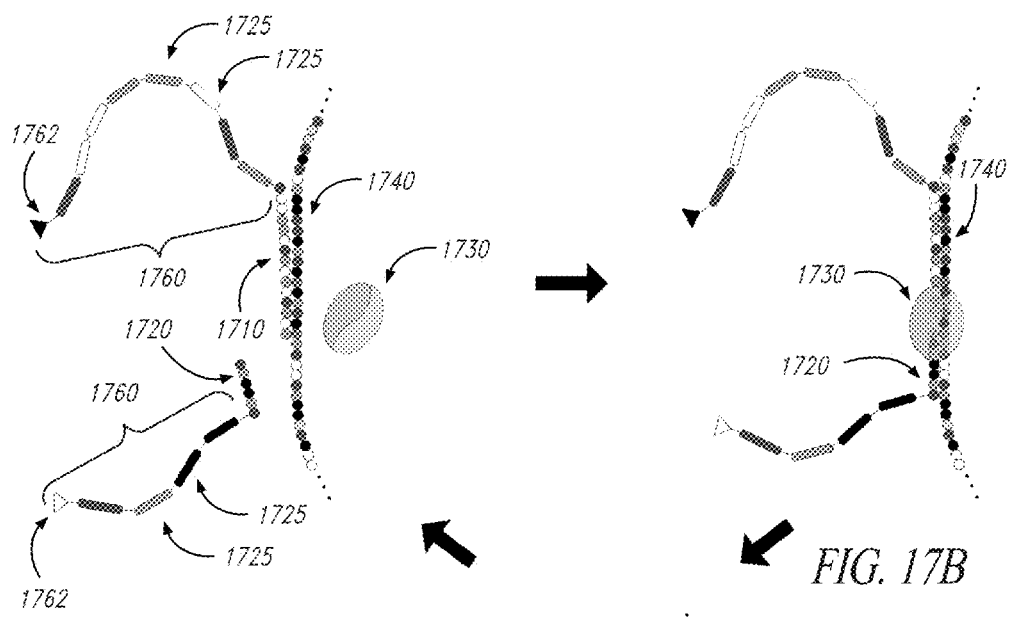
FIG. 17A
FIG. 17B
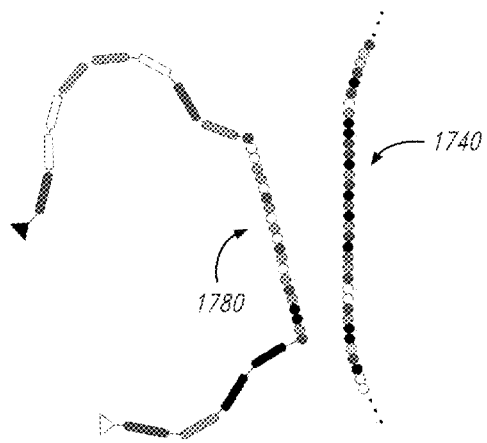
FIG. 17C

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: Oligonucleotide

<400> SEQUENCE: 1
aacgcactca atccatcttc aggt                                            24

<210> SEQ ID NO 2
<211> LENGTH: 24
<212> TYPE: DNA
<213> ORGANISM: Artificial
<220> FEATURE:
<223> OTHER INFORMATION: Oligonucleotide

<400> SEQUENCE: 2
acctgaagat ggattgagtg cgtt                                            24

<210> SEQ ID NO 3
<211> LENGTH: 24
<212> TYPE: DNA
<213> ORGANISM: Artificial
<220> FEATURE:
<223> OTHER INFORMATION: Oligonucleotide

<400> SEQUENCE: 3
aacgcactca atccatcttc aggt                                            24

<210> SEQ ID NO 4
<211> LENGTH: 24
<212> TYPE: DNA
<213> ORGANISM: Artificial
<220> FEATURE:
<223> OTHER INFORMATION: Oligonucleotide
```

```
<400> SEQUENCE: 4
acctgaagat ggattgagtg cgtt                                              24
```

MULTIPLEXED IDENTIFICATION OF NUCLEIC ACID SEQUENCES

CROSS-REFERENCE TO RELATED APPLICATION

The present application claims the benefit under 35 U.S.C. §119(e) of U.S. Provisional Patent Application No. 61/360,385 filed on Jun. 30, 2010, which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 870225_406_SEQUENCE_LISTINGa.txt. The text file is 1 KB, was created on Nov. 22, 2011, and is being submitted electronically via EFS-Web.

BACKGROUND

1. Technical Field

The present invention is generally related to detection of nucleic acid sequences, as well as methods for rapid identification of target sequences in mixed nucleic acid samples.

2. Description of the Related Art

Rapid and accurate detection of nucleic acid sequence has become increasingly important. For example, threats of biological warfare and terrorism impose a need for rapid identification of specific pathogens in samples found on the battlefield, at border crossings, and in the work environment generally. In addition, infectious disease accounts for approximately 7% of human mortality in developed nations, and as much as 40% in the developing world. Rapid and accurate identification of the causative pathogen could result in increased survival of infected patients and enable better containment of outbreaks. Unfortunately, traditional microbiology techniques (e.g., cell culturing) for identifying biological agents can take days or even weeks, often delaying a proper course of action. Antibody based assays can be done quickly and easily, but often lack sensitivity and/or specificity.

A desirable alternative to traditional approaches would have one or more of the following characteristics: high specificity (>99.9%) and sensitivity (<1000 copies); high-level multiplexing (>100 targets); automated sample preparation; fully integrated processes on disposable reagent cartridge; sample-to-result in less than 15 minutes; rapid reconfiguration for addition of new biomarkers; flexible targeting; and/or have an associated compact, low-cost field deployable instrument. Unfortunately, there are currently no technologies on the market that satisfy these criteria.

Probe hybridization arrays can measure a broad spectrum of nucleic acid targets (I. Biran, D. R. Walt, and J. R. Epstein, "Fluorescence-based nucleic acid detection and microarrays," *Analytica Chimica Acta*, vol. 469, no. 1, pp. 3-36.1), but typically have limited sensitivity of $10^5$ to $10^6$ target molecules and are also limited by diffusion and nonspecific binding. Bead-based methods of improving sensitivity to attomolar levels have been devised (J. Nam, S. I. Stoeva, and C. A. Mirkin, "Bio-Bar-Code-Based DNA Detection with PCR-like Sensitivity," *Journal of the American Chemical Society*, vol. 126, no. 19, pp. 5932-5933, May. 2004; S. I. Stoeva, J. Lee, J. E. Smith, S. T. Rosen, and C. A. Mirkin, "Multiplexed Detection of Protein Cancer Markers with Biobarcoded Nanoparticle Probes," *Journal of the American Chemical Society*, vol. 128, no. 26, pp. 8378-8379, July 2006). Bead-based methods to reduce nonspecific signal have also been devised (S. P. Mulvaney et al., "Rapid, femtomolar bioassays in complex matrices combining microfluidics and magnetoelectronics," *Biosensors & Bioelectronics*, vol. 23, no. 2, pp. 191-200, September 2007).

Specificity and sensitivity limitations of probe hybridization methods have been improved by using two probes that hybridize and ligate to produce a single product with unique electrophoretic drag (U.S. Pat. No. 4,883,750). This approach has provided two advantages: (i) the single product helps isolate its signal from other background, and (ii) the specificity of the ligase ensures high fidelity within five bases of the ligation site. Further improvements have involved adding fluorescent identifiers to probes (E. S. Winn-Deen and D. M. Iovannisci, "Sensitive fluorescence method for detecting DNA-ligation amplification products," *Clinical Chemistry*, vol. 37, no. 9, pp. 1522-1523, September 1991; U.S. Pat. No. 5,514,543). Higher information identifiers have been proposed that require amplification in order to obtain sufficient signal to identify the target (PCT Publication WO 2010/115100; U.S. Pat. No. 7,320,865).

DNA sequencing can also be used for the identification of pathogens. Because each pathogen's DNA sequence is unique, sequencing allows for the identification of any number of different pathogens. Currently, most diagnostic DNA sequencing is performed using the chain termination method developed by Frederick Sanger. This technique, termed "Sanger Sequencing," uses sequence specific termination of DNA synthesis and fluorescently modified nucleotide reporter substrates to derive sequence information. However, this method comprises a modified polymerase chain reaction (PCR) which makes this approach time consuming and expensive. Furthermore, PCR cannot simultaneously amplify many pathogen probe targets in a single reaction which requires samples to be split into many parallel reaction paths, increasing complexity and cost while reducing sensitivity. As a result, new sequencing methods, such as products from Illumina (San Diego, Calif.) and Life technologies (Carlsbad, Calif.), are displacing traditional methods. These technologies, however, are still largely reliant on PCR and use expensive and complex equipment that are not appropriate for rapid, low cost on-site detection.

Accordingly, while significant advances have been made in the field of nucleic acid detection generally, there is still a need in this field for techniques and corresponding devices that enhance or otherwise improve on the current state of the art, particularly with regard to sensitivity, specificity, high multiplexing, rapid result time, portability and/or cost. The present invention fulfills some or all of these needs, and provides further related advantages as evident upon review of the attached drawings and following description.

BRIEF SUMMARY

In general terms, methods, corresponding devices, products and kits are disclosed for rapidly and accurately identifying target nucleic acid sequences in sample, such as a mixed nucleic acid sample. Existing methods for pathogen detection are time consuming, thus delaying the time before an appropriate course of action or treatment regimen can begin. In contrast, the disclosed methods, corresponding devices, products and kits methods are sensitive and specific, and capable of rapid detection without the need for PCR amplification.

The disclosed methods are particularly amenable to incorporation in a portable, integrated system with a single reaction and detection channel for rapid identification of a broad spectrum of pathogens. The methods employ probe hybridization and enzymatic ligation to produce single-molecule identifiers, referred to herein as a target identifier, that select specifically for each pathogen's genomic sequence. Each target identifier has a polymeric string of high signal-to-noise reporters to encode one of thousands of possible signatures that can be directly read with a solid-state nanopore or other single molecule detection techniques. The disclosed methods may employ a solution-based approach which incorporates filtering techniques to isolate the target identifier. In addition, the reactions that synthesize and isolate the target identifiers can be completed in a matter of minutes, in preparation for detection. Nanopore detection is a suitable detection technology and is capable of readout rates>1,000 target identifiers/minute, thus providing for rapid and timely detection and identification.

In more specific embodiments, methods are disclosed for identification of a target nucleic acid sequence in a sample, such as a nucleic acid sequence derived from a pathogen. The sample is contacted with a capture probe comprising a sequence of nucleobases complementary to a portion of the target template, and a terminal probe comprising a sequence of nucleobases complementary to a portion of the target template, wherein the sample, the capture probe and the terminal probe are admixed under conditions sufficient to provide for hybridization of the capture probe. Conditions are also provided such that the terminal probe, which is perfectly complementary to template adjacent to the capture probe, is preferentially ligated to the capture probe at temperatures that are above the thermal melting temperatures of the transient probe (typically 4 to 6 bases). This ligation reaction is referred to herein as transient hybridization ligation (THL), and can proceed in either the 5' or 3' direction, or in both the 5' and 3' direction. The resulting ligation product is referred to as target identifier.

In some embodiments, the capture probe comprises a reporter tether. A reporter tether is sufficiently encoded to uniquely identify the capture probe sequence. The reporter tether may directly encode the genetic sequence data or it may encode an identifier which is associated with the actual sequence (for example, through a lookup table). The capture probe generally comprises a sequence of 10-100, or more specifically 20-100 or 20-70, nucleobases complementary to a portion of the target template.

In some embodiments, the terminal probe comprises a reporter tether sufficiently encoded to uniquely identify the terminal probe sequence. The terminal probe generally comprises a sequence of 3-8 nucleobases, or more specifically 4-6, complementary to a portion of the target template.

In some embodiments, the capture probe has no reporter tether and is extended by ligation in both directions with a 3'-extending terminal probe and a 5'-extending terminal probe, both with reporter tethers. The resulting target identifier comprises two reporter tethers, one from each terminal probe.

In some embodiments, a third type of probe, referred to as a nested probe, is employed. It is typically 3-8, or more specifically 4-6, nucleobases in length and extends by THL from the capture probe. One or more nested probes may be further extended by a terminal probe to form the target identifier. The nested probe adds a further level of stringency to the reaction of forming the target identifier, reducing the number of false positives. Such additional THL extension provides increased specificity between the resulting target identifier and the template. In some embodiments the nested probe has no reporter tether and is a limited library of base combinations intended to complement adjacent to capture probes on templates of specific targets.

In other embodiments, the nested probe is what is referred to as an Xprobe as described in published U.S. Patent Application No. US2009/0035777 (incorporated herein by reference in its entirety). After the target identifier is formed, an additional cleavage step breaks a linkage that allows the reporter tether of the Xprobe to linearize and be sequentially detected. In some embodiments a single nested probe is employed, while in other embodiments multiple nested probes are employed.

In other embodiments, the target identifier comprises a reporter tether having a reporter code sufficient to parse the genetic information of the entire target template. In other embodiments, the capture probe, terminal probe, or both, are adapted with linkers, also referred to herein as T-linkers. T-linkers may be irreversible or reversible and they may be selectively linkable or selectively cleavable. T-linkers may be used to tether to solid support, such as magnetic beads, dielectric beads, drag tags or other solid substrates to assist in purification and/or concentration of the target identifier. In these embodiments the target identifier may have one or more, such as two, T-linkers.

In further embodiments, the method further comprises reading the target identifier reporter code, parsing the genetic information of the target template and using the genetic information of the target template to identify the target nucleic acid sequence, such as a biomarker. For example, in further embodiments of the foregoing a detector construct is provided, wherein the detector construct comprises a first and a second reservoir comprising first and second electrodes, respectively, wherein the first and second reservoirs are separated by a nanopore substrate positioned between the first and second reservoirs, the nanopore substrate comprising at least one nanopore channel, and reading the target identifier reporter code comprises translocating the target identifier from the first reservoir to the second reservoir through the at least one nanopore channel. In more particular embodiments, reading the target identifier reporter code further comprises measuring the impedance change along or across the nanopore channel as the target identifier translocates through the nanopore channel. In still other embodiments, the target identifier may be detected using a duplex interrupted method in a biological nanopore (see, e.g., Gundlach et al., *PNAS*, 1001831107, 2010). In other embodiments, the target identifier may be detected by an optical microscope that detects fluorophore reporters.

In other embodiments, the method further comprises capturing, washing and/or concentrating the target identifier.

In other embodiments, a kit is provided that comprises a plurality of probes for detecting any number of nucleic acid biomarkers. For example, such a kit has a library of capture probes, that may contain unique capture probes numbering, for example, from 1 to 10, from 1 to 100 or, in some embodiments, greater than 100, or in some embodiments greater than 1000 or greater than 10000. The kit may also contain a library of terminal probes with unique terminal probes numbering, for example, from 1 to 10, from 1 to 100 or, in some embodiments all possible base combinations (e.g., 256 for 4-base terminal probes). The identity of each probe type may be encoded in its reporter tether.

These and other aspects of the invention will be apparent upon reference to the attached drawings and following detailed description. To this end, various references are set forth herein which describe in more detail certain procedures, compounds and/or compositions, and are hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 17 is a schematic showing various aspects of a method for enhanced target sequence detection using thermal cycling; namely, (a) admixture of a capture probe, a terminal probe, a target nucleic acid and DNA ligase, (b) ligation of the terminal probe to the template, and (c) release of the target identifier.

DETAILED DESCRIPTION

Figure 1:
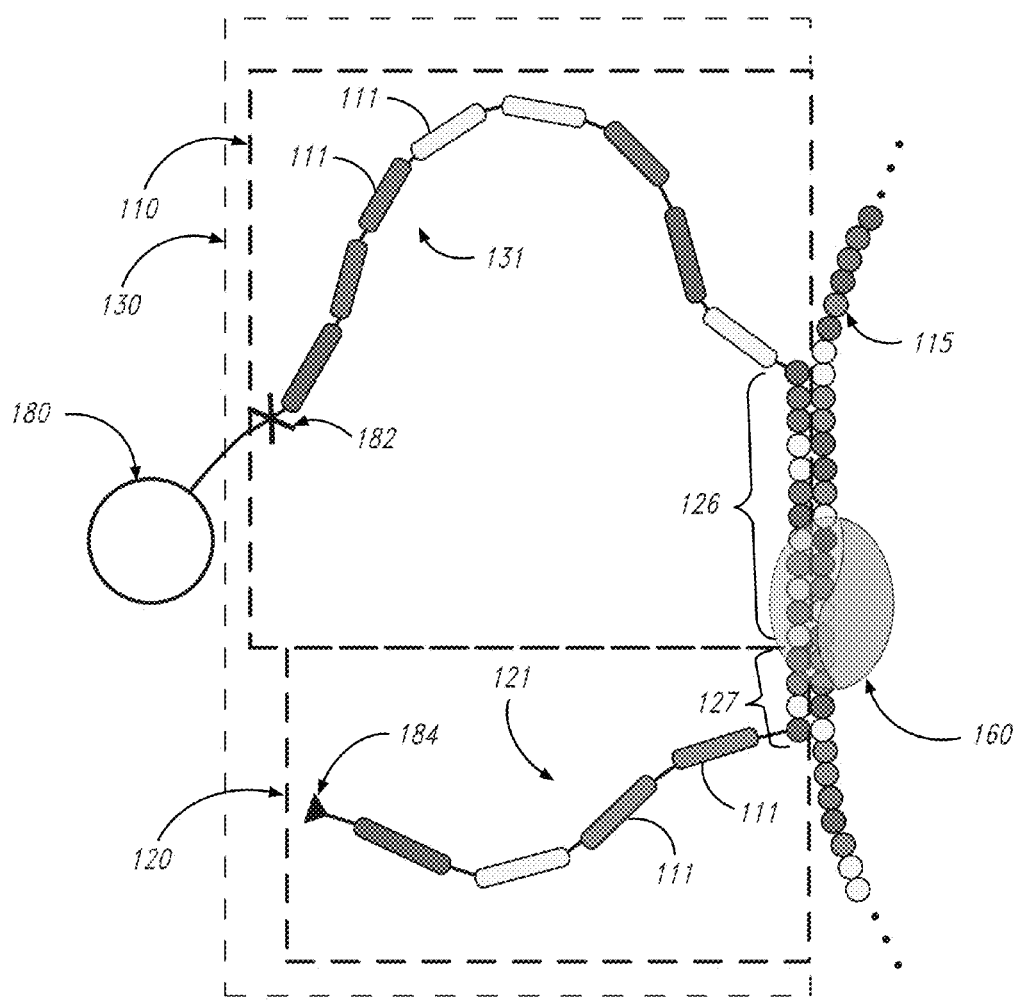
FIG. 1 is a schematic showing ligation of the capture probe and the terminal probe in the presence of the target template to form the target identifier.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

DEFINITIONS

As used herein, and unless the context dictates otherwise, the following terms have the meanings as specified below.

"Analyte nucleic acid" means a nucleic acid which is the subject of analysis and/or detection. Analyte nucleic acids include pathogen nucleic acids as well as other nucleic acids. "Target sequence" or "target template" means the portion of an analyte nucleic acid which is being sequenced. A target template provides unique genetic information such that the source of the analyte nucleic acid can be identified. For example, a target template may be unique to a particular pathogen, thus allowing detection of the same. Selectively cleavable bond" or "selectively cleavable linker" refers to a bond which can be broken under controlled conditions such as, for example, conditions for selective cleavage of a phosphorothiolate bond, a photocleavable bond, a phosphoramide bond, a 3'-O-B-D-ribofuranosyl-2' bond, a thioether bond, a selenoether bond, a sulfoxide bond, a disulfide bond, deoxyribosyl-5'-3' phosphodiester bond, or a ribosyl-5'-3' phosphodiester bond, as well as other cleavable bonds known in the art. A selectively cleavable bond can be an intra-tether bond or between or within a probe or a nucleobase residue or can be the bond formed by hybridization between a probe and a template strand. Selectively cleavable bonds are not limited to covalent bonds, and can be non-covalent bonds or associations, such as those based on hydrogen bonds, hydrophobic bonds, ionic bonds, pi-bond ring stacking interactions, Van der Waals interactions, and the like.

"Bio-threat agent" is a pathogen used as a weapon, for example in warfare or terrorism. Examples of bio-threat agents include anthrax, smallpox, plague and tularemia.

"Capture probe" refers to a probe which selectively hybridizes to a target template to form a primer for extension ligation. Capture probes are generally comprised a single-stranded portion of 10-100 nucleobases that is complementary to the target template of interest. In some embodiments, the capture probe further comprises a reporter tether that is sufficiently encoded to uniquely identify the capture probe sequence; namely, the capture probe comprises a reporter tether having a reporter code sufficient, upon detection, to parse the genetic information of all or a portion of the target nucleic acid sequence to which the capture probe is complementary. In some embodiments, the capture probe is tethered to a solid support by a selectively cleavable linker, or comprises a reversible linker for tethering to a solid support, or more generally comprises a T-linker.

"Complementary" generally refers to specific nucleotide duplexing to form canonical Watson-Crick base pairs, as is understood by those skilled in the art. However, complementary as referred to herein also includes base-pairing of nucleotide analogs, which include, but are not limited to, 2'-deoxyinosine and 5-nitroindole-2'-deoxyriboside, which are capable of universal base-pairing with A, T, G or C nucleotides and locked nucleic acids, which enhance the thermal stability of duplexes. One skilled in the art will recognize that hybridization stringency is a determinant in the degree of match or mismatch in the duplex formed by hybridization.

"Detector" is an apparatus used for detection of probes. Detector constructs include any element necessary for detection of the probes, and generally comprise at least one detector element. The detector element is capable of detecting reporter elements. Examples of detector elements include, but are not limited to, a nanopore channel, fluorescence detectors, UV detectors, chemical and electrochemical detectors, photoelectric detectors, and the like. Detector constructs may have elements that function to resolve reporter signals.

"Encode" is a verb referring to transferring from one format to another and typically referring to transferring the genetic information of oligomer probe base sequence into an arrangement of reporters.

"Fluorophore" is a fluorescent molecule or a component of a molecule that causes the molecule to be fluorescent. Fluorescein is a non-limiting example of a fluorophore.

"Indicator" means a moiety, for example a chemical species, which can be detected under the conditions of a particular assay. Non-limiting examples of indicators and reporters moieties include: fluorophores, chemiluminescent species, and any species capable of inducing fluorescence or chemiluminescence in another species.

"Ligase" is an enzyme generally for joining 3'-OH 5'-monophosphate nucleotides, oligomers, and their analogs. Ligases include, but are not limited to, NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase I, DNA ligase III, DNA ligase IV, and novel ligases discovered by bioprospecting. These ligases include wild-type, mutant isoforms, and genetically engineered variants.

"Ligation" or "ligate" refers to joining 3'-OH 5'-monophosphate nucleotides, oligomers, and their analogs.

"Linker" is a molecule or moiety that joins two molecules or moieties, and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., *Nucleic Acids Res.* 27: 4416-4426, 1999). Methods of derivatizing and coupling organic molecules are well known in the arts of organic and bioorganic chemistry. A linker may also be cleavable or reversible. Under some circumstances a hybridizable oligomer can be considered a linker when it duplexes to its complementary oligomer.

"Melting temperature" or "Tm" refers, in the case of DNA molecules, to the temperature at which half of the DNA stands are in the double-helical state and half are in the random coil states. The melting temperature depends on both the length of the molecule, and the specific nucleotide sequence composition of that molecule (*Proc. Natl. Acad. Sci. USA* 95 (4): 1460-5).

"Moiety" is one of two or more parts into which something may be divided, such as, for example, the various parts of a tether, a molecule or a probe.

"Nested probe" refers to a probe which transiently hybridizes to a target template and ligates to a capture probe or the ligated extension of a capture probe. Nested probes generally comprise from 3-8 nucleobases and may be ligated at both ends. Nested probe may have no reporter tether (as in the case of a simple probe), or may have a reporter tether (as in the case of an Xprobe).

"Nucleic acid" is a polynucleotide or an oligonucleotide. A nucleic acid molecule can be deoxyribonucleic acid (DNA), ribonucleic acid (RNA), or a combination of both. Nucleic acids can be mixtures or pools of molecules targeted for sequencing. Nucleic acids are generally referred to as "target nucleic acids" or "target sequences". A "target template" is the portion of a target nucleic acid to which the Capture Probe and Terminal Probe hybridize and provides unique genetic information such that the source of the target nucleic acid can be identified. For example, a target template may be unique to a particular pathogen thus allowing detection of the same.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and published PCT applications WO 92/002258, WO 93/10820, WO 94/22892 and WO 94/24144, and Fasman ("Practical Handbook of Biochemistry and Molecular Biology", pp. 385-394, 1989, CRC Press, Boca Raton, La.), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Parse" or "Decode" are verbs referring to transferring from one format to another, typically referring to transferring an arrangement of reporters or the associated reporter code into a probe identification number or into genetic information of probe base sequence (or the nucleic acid to which it is complementary).

"Pathogen" is a biological agent that can cause disease to its host. Pathogens include, but are not limited to, viruses, bacteria, fungi, parasites, prions and the like. Exemplary pathogens include viruses from the families of: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae and Togaviridae. Exemplary bacteria include *Mycobacterium tuberculosis, Streptococcus, Pseudomonas, Campylobacter, Salmonella, E. coli* and the like.

"Polynucleotides", also called nucleic acids or nucleic acid polymers, are covalently linked series of nucleotides. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound, having a linear backbone of nucleotides. Oligonucleotides, also termed oligomers, are generally shorter chained polynucleotides.

"Probe" is a short strand of nucleobase residues, referring generally to two or more contiguous nucleobase residues which are generally single-stranded and complementary to a target sequence of a nucleic acid. Probes may be chimeric and may include DNAs, RNAs, PNAs and LNAs. Probes may include modified nucleobase residues and modified intranucleobase bonds in any combination. Backbones of probes can be linked together by any of a number of types of covalent bonds, including, but not limited to, ester, phosphodiester, phosphoramide, phosphonate, phosphorothioate, phosphorothiolate, amide bond and any combination thereof. The probe may also have 5' and 3' end linkages that include, but are not limited to, the following moieties: monophosphate, triphosphate, hydroxyl, hydrogen, ester, ether, glycol, amine, amide, and thioester.

"Reading", within the context of reading a reporter element or reporter construct, means identifying the reporter element or reporter construct. The identity of the reporter element or reporter construct can then be used to decode the genetic information of the target nucleic acid.

"Reporter" or "reporter element" is a signaling element, molecular complex, compound, molecule or atom that is also comprised of an associated "reporter detection characteristic". Reporter elements include what are known as "tags" and "labels," and serve to parse the genetic information of the target nucleic acid. Reporter elements include, but are not limited to, FRET resonant donor or acceptor, dye, quantum dot, bead, dendrimer, up-converting fluorophore, magnet particle, electron scatterer (e.g., boron), mass, gold bead, magnetic resonance, ionizable group, polar group, hydrophobic group. Still others are fluorescent labels, such as but not limited to, ethidium bromide, SYBR Green, Texas Red, acridine orange, pyrene, 4-nitro-1,8-naphthalimide, TOTO-1, YOYO-1, cyanine 3 (Cy3), cyanine 5 (Cy5), phycoerythrin, phycocyanin, allophycocyanin, FITC, rhodamine, 5(6)-carboxyfluorescein, fluorescent proteins, DOXYL (N-oxyl-4,4-dimethyloxazolidine), PROXYL (N-oxyl-2,2,5,5-tetramethylpyrrolidine), TEMPO(N-oxyl-2,2,6,6-tetramethylpiperidine), dinitrophenyl, acridines, coumarins, Cy3 and Cy5 (Biological Detection Systems, Inc.), erytrosine, coumaric acid, umbelliferone, texas red rhodaine, tetramethyl rhodamin, Rox, 7-nitrobenzo-1-oxa-1-diazole (NBD), oxazole, thiazole, pyrene, fluorescein or lanthamides; also radioisotopes (such as $^{33}P$, $^{3}H$, $^{14}C$, $^{35}S$, $^{125}I$, $^{32}P$ or $^{131}I$), ethidium, Europium, Ruthenium, and Samarium or other radioisotopes; or mass tags, such as, for example, pyrimidines modified at the C5 position or purines modified at the N7 position, wherein mass modifying groups can be, for examples, halogen, ether or polyether, alkyl, ester or polyester, or of the general type XR, wherein X is a linking group and R is a mass-modifying group, chemiluminescent labels, spin labels, enzymes (such as peroxidases, alkaline phosphatases, beta-galactosidases, and oxidases), antibody fragments, and affinity ligands (such as an oligomer, hapten, and aptamer). Association of the reporter element with the tether can be covalent or non-covalent, and direct or indirect. Representative covalent associations include linker and zero-linker bonds. Included are bonds to the tether backbone or to a tether-bonded element such as a dendrimer or sidechain. Representative non-covalent bonds include hydrogen bonds, hydrophobic bonds, ionic bonds, pi-bond ring stacking, Van der Waals interactions, and the like. Ligands, for example, are associated by specific affinity binding with binding sites on the reporter element.

"Reporter code" includes the genetic information from a measured signal of a reporter tether. The reporter code is decoded to provide sequence-specific genetic information data. It may also include information to assist in error detection such as parity, or information to determine code direction, or other functional information to improve decoding performance.

"Reporter detection characteristic" referred to as the "signal" describes all possible measurable or detectable elements, properties or characteristics used to communicate the genetic sequence information of a reporter directly or indirectly to a measurement device. These include, but are not limited to, fluorescence, multi-wavelength fluorescence, emission spectrum fluorescence quenching, FRET, emission, absorbance, reflectance, dye emission, quantum dot emission, bead image, molecular complex image, magnetic susceptibility, electron scattering, ion mass, magnetic resonance, molecular complex dimension, molecular complex impedance, molecular charge, induced dipole, impedance, molecular mass, quantum state, charge capacity, magnetic spin state, inducible polarity, nuclear decay, resonance, or complementarity.

"Reporter tether" or "reporter construct" is a tether comprising one or more reporters that can produce a detectable signal(s), wherein the detectable signal(s) generally contain sequence information. This signal information is termed the "reporter code" and is subsequently decoded into genetic sequence data. A reporter tether may also comprise tether segments or other architectural components including nucleic acids, polymers, graft copolymers, block copolymers, affinity ligands, oligomers, haptens, aptamers, dendrimers, linkage groups or affinity binding group (e.g., biotin).

"Selective hybridization" refers to specific complementary binding. Polynucleotides, oligonucleotides, probes, nucleobase residues, and fragments thereof selectively hybridize to target nucleic acid sequences, under hybridization and wash conditions that minimize nonspecific binding. As known in the art, high stringency conditions can be used to achieve selective hybridization conditions favoring a perfect match. Conditions for hybridization such as salt concentration, temperature, detergents, PEG, and GC neutralizing agents such as betaine can be varied to increase the stringency of hybridization, that is, the requirement for exact matches of C to base pair with G, and A to base pair with T or U, along a contiguous strand of a duplex nucleic acid. Generally, decreasing the salt and increasing the temperature of a hybridization reaction above the Tm of the perfectly matched nucleic acid duplex increases the hybridization stringency and therefore increases the selectivity of said duplex. Selective hybridization generally occurs at or above the Tm. Selective hybridization can be enhanced by capturing and washing said duplex under conditions at which perfectly matched duplex will be stable and mismatched duplexes will be unstable. This can generally be achieved with wash conditions below the Tm of the perfectly matched duplex.

"Solid support" or "solid substrate" is a solid material having a surface for attachment of molecules, compounds, cells, or other entities. The surface of a solid support can be flat or not flat. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, polystyrene, polypropylene, polycarbonate, or polyallomer. A solid support can also be a bead, resin or particle of any shape. Such particles or beads can be comprised of any suitable material, such as glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron. Solid supports may be flexible, for example, a polyethylene terephthalate (PET) film.

"Target identifier" is a product resulting from the contacting and ligation steps of the various methods disclosed herein. Detection of the target identifier allows for identification of the target nucleic acid sequence in the sample. For example, a representative target identifier is formed by ligating a capture probe with a terminal probe, each of which has a reporter tether.

"Terminal probe" refers to a probe which transiently hybridizes to a target template and ligates to a capture probe or the ligated extension of a capture probe. The terminal probe is perfectly complementary to template adjacent to the capture probe, is preferentially ligated to the capture probe at temperatures that are above the thermal melting temperatures of the terminal probe (typically 4 to 6 bases or more generally 3 to 8 bases). In some embodiments, the capture probe further comprises a reporter tether that is sufficiently encoded to uniquely identify the terminal probe sequence; namely, the terminal probe comprises a reporter tether having a reporter code sufficient, upon detection, to parse the genetic information of the portion of the target nucleic acid sequence to which the terminal probe is complementary. In some embodiments, the terminal probe is tethered to a solid support by a selectively cleavable linker, or comprises a reversible linker for tethering to a solid support, or more generally comprises a T-linker.

"Tether" is a polymer having a generally linear dimension with two terminal ends, where the ends form end-linkages for concatenating the tether elements. Reporter Tethers provide a scaffolding for reporter elements. Tethers can include, but are not limited to: polyethylene glycols, polyglycols, polypyridines, polyisocyanides, polyisocyanates, poly(triarylmethyl) methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

"T-linker" is a linker that is used primarily to assist in purification and/or concentration of analyte. T-linkers may be used to tether to magnetic beads, dielectric beads, drag tags or other solid substrates. Depending upon the process an analyte may have more than one T-linker. T-linkers may be irreversible or reversible linkers and they may be selectively linkable or selectively cleavable.

"Transient hybridization" refers to an unstable duplexing of nucleic acids that can be controlled by adjusting the stringency of the hybridization environment. Increasing temperature and decreasing the salt in a hybridization reaction generally increases the stringency of the hybridization reaction. Short oligomer nucleic acid probes hybridized to its reverse complement at a temperature 5° C. above the thermal melting temperature of the duplex will have a much higher degree of transience than the same hybridization reaction carried out at 5° C. below the melting temperature of the probe. Generally, the higher the temperature is above the thermal melting temperature of the nucleic acid duplex, the more unstable or transient the duplex is.

"Transient hybridization ligation" or "THL" is a ligation process used to extend a stable duplex on a nucleic acid template at temperatures that are above the thermal melting temperatures of the extending probe. Template-dependant extension of the stable duplex proceeds by ligating the transiently hybridized probe (e.g., a terminal probe or nested probe). Under these conditions, promiscuous ligation side reactions between the extending probes are suppressed, reducing background detection events and improving assay performance. Generally, THL is performed at temperature greater than the Tm of the hybridizing probe.

"Xpandomer" or "Xpandomer product" is a synthetic molecular construct produced by expansion of a constrained Xpandomer (an Xpandomer prior to cleavage of the selectively cleavable bond), which is itself synthesized by template-directed assembly of substrate constructs. The Xpandomer is elongated relative to the target template it was produced from. It is composed of a concatenation of subunits, each subunit a motif, each motif a member of a library, comprising sequence information, a tether and optionally, a portion, or all of the substrate, all of which are derived from the formative substrate construct. The Xpandomer is designed to expand to be longer than the target template thereby lowering the linear density of the sequence information of the target template along its length. Xpandomers comprise reporter constructs which comprise all the sequence information of the Xpandomer. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand (U.S. Pat. No. 7,939,259).

"Xprobe" is an expandable oligomeric substrate construct. Each Xprobe has a probe member and a tether member. The tether member generally having one or more reporter constructs. Xprobes with 5'-monophosphate modifications are compatible with enzymatic ligation-based methods for Xpandomer synthesis. Xprobes with 5' and 3' linker modifications are compatible with chemical ligation-based methods for Xpandomer synthesis. Xprobes have a selectively cleavable bond that enables expansion (U.S. Pat. No. 7,939,259).

In general terms, methods, corresponding devices and products are disclosed for rapid and accurate identification of target nucleic acid sequences within a sample mixture that may include nucleic acids or other biomarkers of interest. For example, in one embodiment the disclosed methods may be used for detection, identification and quantification of biothreat agents. In another embodiment, the disclosed methods may be used for detection, identification and quantification of an infective agent in a patient sample. In another embodiment, the disclosed methods may be used for diagnostic and therapeutic applications related to cancer, autoimmune diseases, obesity and the like, including associated drug efficacy and toxicity assessment.

Such rapid and accurate methods for detection of biomarkers allow for treatment and/or corrective action on a timescale not obtainable when more traditional means of identification are employed. For example, the ligation approach disclosed herein provides for high specificity, as well as run times of less than 15 minutes. In addition, the disclosed methods allow for single molecule detection of less than 1000 target copies without the need for PCR amplification. The sensitivity can be further enhanced by using multiple probe targets for each genomic target and by making multiple Target Identifiers from each target template with thermal cycling (linear amplification). Additionally, the high multiplexing capability of simultaneously interrogating a sample for thousands of different possible pathogens decreases cost-per-pathogen tested and reduces sampling requirements. Furthermore, the tests are extendable by simply adding new probes to the libraries in an ongoing basis as necessary or useful.

In addition to high sensitivity and speed, the methods are extendable by integration of sequence by expansion methods (SBX) (U.S. Pat. No. 7,939,259). Because the methods are solution-based with total waste reagent of <1.0 ml/run they are amendable to compact, portable (e.g., handheld) analysis. Furthermore, hybridization and ligation methods are configurable to be highly specific. Single molecule measurement can provide thousands of biomarker identifiers/minute making the assays robust and redundant. These and other related advantages are apparent in reference to the following discussion.

In one embodiment, a method for identifying a target nucleic acid sequence in a sample is disclosed. The method comprises contacting the sample with a capture probe and a first terminal probe under conditions that provide for selective hybridization of the capture probe to a first portion of the target nucleic acid sequence, and transient hybridization of the first terminal probe to a second portion of the target nucleic acid sequence adjacent to the first portion of the target nucleic acid sequence; ligating the capture probe and the first terminal probe to form a target identifier; and detecting the target identifier and thereby identifying the target nucleic acid sequence in the sample. The target nucleic acid sequence may be derived from a pathogen, and detecting the target identifier identifies the pathogen.

In another embodiment, the method comprises identifying a target nucleic acid sequence in a sample by contacting the target nucleic acid sequence with a capture probe under conditions that provide for selective hybridization of the capture probe to a first portion of the target nucleic acid sequence, wherein the capture probe comprises a reporter tether and a probe complementary to the first portion of the target nucleic acid sequence; ligating a terminal probe to the capture probe under conditions that provide for transient hydridization of the terminal probe to a second portion of the target nucleic acid sequence adjacent to the first portion of the target nucleic acid sequence to form a target identifier, wherein the terminal probe comprises a reporter tether and a probe complementary to the second portion of the target nucleic acid sequence; and detecting the target identifier and thereby identifying the target nucleic acid sequence in the sample.

The probe of the capture probe may comprise from 10 to 100 nucleobases. The capture probe may be tethered to a solid support by a linker (e.g., selectively cleavable linker), or comprises a linker (e.g., reversible linker) for tethering to a solid support. The reporter tether of the capture probe may comprise a reporter code that, upon detection, parses the genetic information of the first portion of the target nucleic acid sequence to which the probe of the capture probe is complementary.

The probe of the terminal probe may comprise from 3 to 8 nucleobases. The terminal probe may be tethered to a solid support by a linker (e.g., selectively cleavable linker), or comprises a linker (e.g., reversible linker) for tethering to a solid support. The reporter tether of the terminal probe may comprise a reporter code that, upon detection, parses the genetic information of the second portion of the target nucleic acid sequence to which the probe of the terminal probe is complementary.

The target nucleic acid sequence may be contacted with a plurality of capture probes, wherein the probe of each capture probe is complementary to a different target nucleic acid sequence. The plurality of capture probes may be greater than 10, greater than 100, or greater than 1000.

The step of ligating the terminal probe to the capture probe may comprise exposing the second portion of the target nucleic acid sequence to a plurality of terminal probes having probes with different combinations of nucleobases. The plurality of terminal probes having probes with different combinations of nucleobases may be greater than 10, greater than 50, greater than 100, greater than 200, or greater than 1000.

The method may further comprise at least one step of capturing, washing and concentrating the target identifier prior to detection. The step of detecting may be accomplished by translocating the target identifier through a nanopore. The target identifier may be amplified prior to detection by, for example, polymerase chain reaction (PCR) or by thermal cycling.

Figures 2A, 2B:
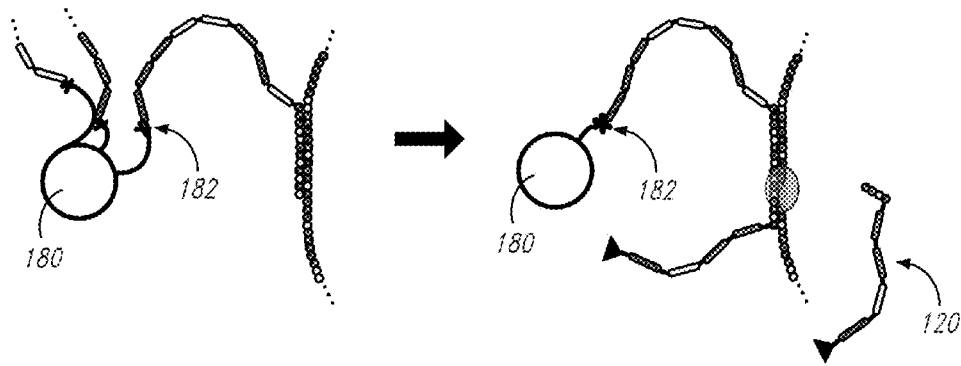
FIG. 2 is a schematic showing various aspects of the disclosed method; namely, (a) selective hybridization of the capture probe, (b) transient hybridization and ligation of the terminal probe, (c) extraction of the target identifier and cleavage of the first bead, (d) capture of the target identifier by a second bead, and (e) release and detection of the target identifier.
Figures 2C, 2D:
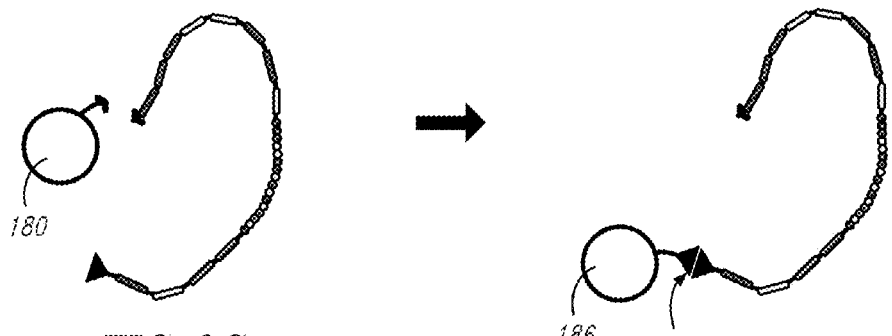
Figure 2E:
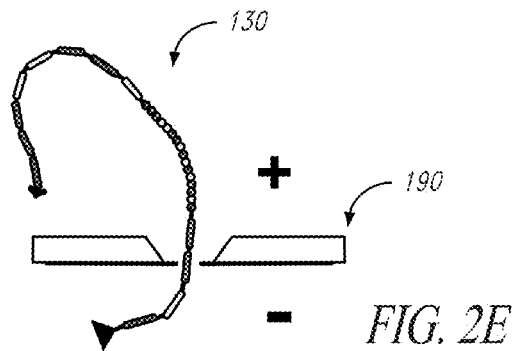

FIGS. 1 and 2 depict one embodiment of the disclosed methods and related products. In this embodiment, the method employs two labeled oligonucleotide probes, the capture probe (110) and the terminal probe (120), to produce a single-molecule identifier specific to a target template (115) called the target identifier (130). In the presence of a target nucleic acid having a unique target template (e.g., a virulence factor of a target pathogen), probe (126) of capture probe (110) selectively hybridizes on the target template (115) to form a stable duplex (referred to herein as selective hybridization). Next, probe (127) of terminal probe (120) transiently hybridizes to the template adjacent to the capture probe and is enzymatically ligated via ligase (160) to form a measurable product called a target identifier (130). Only if a target template is present in the test sample will the capture probe and terminal probe form a target identifier, thus confirming the presence of the target nucleic acid.

As illustrated in FIGS. 1 and 2, both the capture probe (110) and the terminal probe (120) have reporters, depicted as discrete units (111). The reporters encode reporter codes along their respective reporter tethers (131, 121) (i.e., a capture probe reporter code and a terminal probe reporter code). When the capture probe and terminal probe are ligated their respective reporter codes combine to comprise the target identifier reporter code which uniquely identifies the targeted template. In this embodiment, the capture probe is tethered to a magnetic bead (180) by a cleavable linker (182). This is used to wash and purify the target identifier. Next the beads, which may have multiple capture probes linked thereto, are cleaved and the purification product is purified a second time using the reversible linker (184), such as a T-linker, with a second magnetic bead (186) (shown in FIG. 2) having the appropriate linker receptor (187). In this second purification only the target identifier will link to the bead and be selected. This double purification strategy helps reduce detector background events and to concentrate the target identifiers. The final step in this embodiment, depicted in FIG. 2, shows a target identifier passing through a Coulter-like nanopore detector (190). Impedance-based reporters positioned serially along the target identifier are identified as they pass through the nanopore. This series of identities is the target identifier reporter code and is used to identify the target template.

In some embodiments, each capture probe comprises an oligomer probe (10 to 100 bases), a reporter tether and a T-linker, and each terminal probe comprises an oligomer probe (3 to 8 bases), a reporter tether and a second T-linker. The reporter tethers are attached distal to the ligating end of the capture probe and terminal probe (via a base modification) and comprise a serial string of reporters, each of which is designed for measurement in the detector construct. The T-linkers are designed to provide attachments for a first and a second serial purification, each purification selecting for product that is comprised of one of the T-linkers. After both purifications only the product that comprises both T-linkers is recovered (i.e., the process selects for only target identifiers).

The oligomer portion of the terminal probe is shorter than that of the capture probe and has a thermal melt temperature (Tm) below the temperature (T) at which the ligation is performed. This T-Tm differential suppresses promiscuous priming by the terminal probe and preferentially ligates to the hybridized capture probe is the dominant ligation product (target identifier). This type of ligation is called Transient Hybridization Ligation (THL). Under THL conditions, a terminal probe that is complementary to the template will not form a stable duplex, but will hybridize transiently and (with ligase) will selectively ligate to extend the stable duplex. THL suppresses promiscuous ligation side reactions that lead to undesirable background, but also promotes higher fidelity ligation. THL may be performed where T-Tm is >1° C. or >5° C. or >20° C.

In some embodiments, the reporter tether for the terminal probe can be a simple label to identify the target identifier as ligated, or it can carry additional sequence information to provide variant information. For example, in some further embodiments, a single capture probe can be ligated to two terminal probes (and thus two different reporter codes) in a target dependant manner. As such the target identifier product informs on the identity of two distinct loci. Alternatively, in another embodiment all 256 tetramer terminal probes (with all possible 4-base combinations) are used with each capture probe to identify all possible 4-mer variants in the ligated portion of the target identifier.

In some other embodiments, each reporter has a minimum of two states for encoding the base sequence information or an identification number. For example, three 4-state reporters encode for a three-base probe sequence. In still another example, six 4-state reporters encode for 4096 identification numbers. Parity or error correction information may also be encoded in the reporters. For example, in one specific embodiment, 9 binary-state reporters encode a 4 base sequence (2 bits/base) of the associated probe and use the last reporter to encode parity of the previous 8 bits to improve detection read fidelity. In other embodiments, the code directionality is indicated to eliminate the read direction ambiguity. For example, probe reporter codes can be designed so when they combine to form the target identifier reporter code, there is always a low state at the start of the code and a high state at the end of the code, thus providing the correct direction to read.

In an N-multiplexed assay, there are N biomarker targets that are simultaneously detected for by detecting for N unique target identifiers. The target identifier reporter code is generally comprised of at least 2 or more reporter code portions that are contributed by the constituent probes. In some embodiments of an N-multiplexed assay, each of the N target identifiers is formed by ligating one of N unique capture probes and one of N unique terminal probes. The reporter codes associated with each probe can be selected to get an unambiguous detection, but may provide different levels of functionality. For example, a robust approach may use N capture probe reporter codes and N terminal probe reporter codes. These produce $N^2$ possible combinations for the target identifier reporter codes of which only N are used. This provides additional stringency for reducing false positives. Alternatively N capture probe reporter codes may be used with a single reporter code associated with all N terminal probes to indicate a successful ligation occurred. In still other examples a combinatorial approach may be used whereby the same reporter code may be associated with different capture probes (or different terminal probes). In this case, multiple possible ligation products may have the same code. In other embodiments, multiple target identifiers may share the same capture probe or the same terminal probe and thus portions of their reporter codes are the same For multiplexed assays, probe libraries can be constructed that will ligate to form any of N unique target identifiers in the presence of any of N nucleic acid targets (or any combination thereof). Capture probe libraries may have >10 unique probes, or may have >100 unique probes, or even >1000 unique probes. Terminal probe libraries may have >10 unique probes, or may have >50 unique probes or may have >100 unique probes, or even >250 unique probes. These target identifiers are purified (optional) and detected to identify and quantify these targets. In some embodiments, multiplexed assays will target N>10 nucleic acid biomarkers. In some embodiments, multiplexed assays will target N>100 nucleic acid biomarkers. In some embodiments, multiplexed assays will target N>1,000 nucleic acid biomarkers. In other embodiments, multiplexed assays will target N>10,000 nucleic acid biomarkers.

Figure 3:
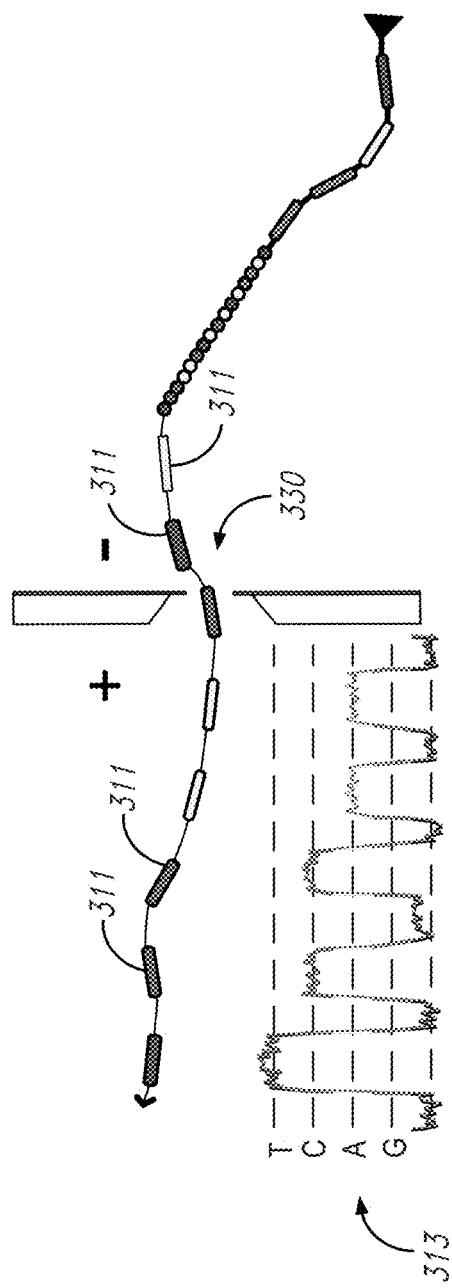
FIG. 3 shows a representative nanopore detector response as a target identifier translocates a solid-state nanopore.

One exemplary method for detection of the target identifier reporter code is the Coulter-like nanopore process illustrated in FIG. 3. Reporters (311) of sufficient size are readily detected and discriminated in solid-state nanopore (330). The nanopore connects two reservoirs that are filled with an aqueous electrolyte solution, typically 1 molar KCl (not shown). A potential is applied between Ag/AgCl electrodes located in each reservoir and a current flows through the nanopore. Typically, the target identifier probe has a negative charge density along its length, and is drawn into and pulled through (translocated) the nanopore by electrophoretic forces. The nanopore current is modulated by whatever portion of the target identifier probe that lies within the nanopore channel. Each reporter type has a unique molecular structure based upon size and/or charge distribution. As each reporter passes through the nanopore, its molecular characteristics alter the current amplitude so the associated reporter identity can be determined. For example, the reporters depicted in FIG. 3 produce 3 of 4 possible current-blocking amplitude levels, each one identifying a different base (313). By capturing this current signal, the sequence information encoded in the Target Identifier reporter code is decoded. Other methods for single-molecule detection and presentation of probes and reporters are disclosed in WO 2008/157696, WO 2009/055617 and PCT/US10/22654 which are hereby incorporated in their entireties.

Accordingly, after purification, target identifiers may be translocated through a nanopore detector which simultaneously quantifies and identifies the spectrum of nucleic acid targets present in a sample based upon a large library of possible targets. In this manner, the reporter code is determined and the genetic sequence of the target template identified. The nanopore detector is capable of single molecule detection of target identifier molecules at rates in excess of 1,000 identifiers/min. Thus, with suitable sample input volume, the detection method identifies low copy number nucleic acid biomarkers without the use of PCR.

Nanopore reporters are molecular constructs designed to create high signal-to-noise current blockages as they translocate through a nanopore. In general, the type (e.g. level of impedance) and positioning (sequential order) of the reporters on the reporter tether determines the identity (i.e., sequence) of the associated probe. In one embodiment, a string of twenty, 2-level reporters provides 20-bits of information and can be used to encode >1 million unique identifiers. In other embodiments, encoding techniques of the telecommunications industry such as matched filters, parity, and CRC codes are used for robust, low-error decryption.

Figure 4:
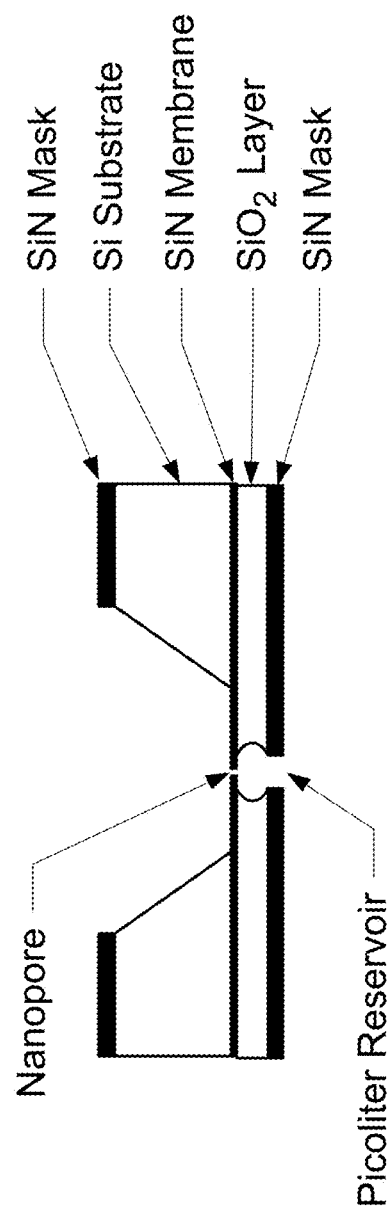
FIG. 4 shows a low noise solid-state nanopore membrane with a picoliter reservoir.

The nanopore detector depicted in FIG. 4 is capable of single-molecule detection and has no fundamental sensitivity limitation. Practically, it is limited by efficiency of guiding the target identifiers into the nanopore. However, in some embodiments, the target identifier is concentrated appropriately such that the nanopore can detect <1000 copies of a target with no PCR pre-amplification. To achieve this level of sensitivity the target identifier sample is confined to a small volume in the nanopore sample input reservoir. For example, in a further embodiment picoliter input reservoirs integrated within each nanopore chip are employed.

Another method of increasing sensitivity and mitigating losses of the target identifiers, such as nonspecific absorption, is to use molecular amplification. Direct PCR amplification of the target sample is limited by the level of multiplexing that can be used due to the amplification bias that skews product populations. However, single molecule detection can eliminate the need for amplification or, in some embodiments, reduce amplification requirements by orders of magnitude, making amplification methods practical. Also important, amplification techniques disclosed here are amenable to high multiplexing.

In some embodiments, the target identifiers are linearly amplified by thermal cycling the ligation reaction between the THL temperature and the melting temperature of the target Identifier to denature it from its template complement. This process is a linear amplification of target identifier provided the ligation products are at low concentration relative to the probe reactants and do not significantly interfere with the ongoing ligation.

In other embodiments, PCR amplification is performed after the target identifier has been produced and purified. In this case, the target identifiers are designed to be contiguous, single-stranded nucleic acid, thus enabling amplification with polymerase. Since the amplicons are nucleic acids, reporters that utilize this amplification strategy are typically encoded using specific nucleotide sequences. The sequences may themselves be the reporter and thus require no further modification prior to measurement or they may be duplexed with complementary probes that are functionalized with sequence specific reporters. The PCR reaction may be either a linear amplification (using a primer specific to only one end of the target identifier) or an exponential amplification (using primers specific to both ends of the target identifier). Amplification of the purified target identifier products can be multiplexed to a very high degree with no significant bias because the reporters and primers are universal structures that comprise most of the amplicon. In some embodiments multiplex amplification of >100 unique target identifiers is provided. In some embodiments multiplex amplification of >1,000 unique target identifiers is provided. In some embodiments multiplex amplification of >10,000 unique target identifiers is provided.

Figure 5:
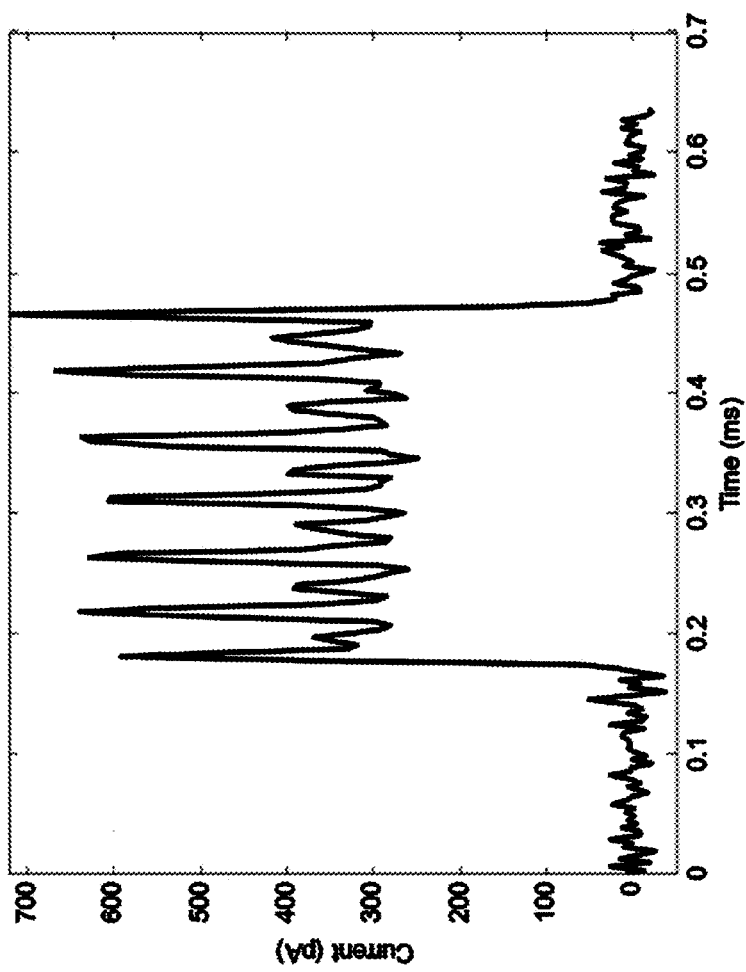
FIG. 5 shows a recorded trace of a 2-state reporter tether translocated through a solid-state nanopore.

FIG. 5 is a time trace that records the current measurement caused by a synthetic 13-peak, 2-state reporter tether passing through a solid-state nanopore. This was recorded with a 100 kHz bandwidth filter on an Axopatch 200B amplifier, and demonstrates reporter resolution<25 μs/reporter. The tether has a ds-DNA backbone with reporters spaced at 600 base intervals. Within each interval, 210 bases have short side-chain oligomers attached at every 10 bases. Alternating reporters have side-chain lengths of 10 and 20 bases that result in two peak heights. Note that using thirteen 2-state reporters provides for >8000 ($2^{13}$) possible identification codes.

In some embodiments the target identifier has two reversibly and selectively linkable T-linkers and is purified with the following method. In a first purification the first T-linker of the target identifier is linked to a magnetic bead or other solid substrate and the beads are washed to remove unbound products. These products, including the target identifiers, are then released. In a second purification the second T-linker of the target identifier is linked to a second magnetic bead type or a second other solid substrate and a second wash step is applied. This purified product is then released for detection.

Only products that comprise both the first and second T-linkers are selected. By design this selects for only the target identifiers.

In some embodiments, post-ligation purification of the target identifier is simplified by tethering the distal end of the capture probe to a magnetic bead via a selectively cleavable linker (e.g., T-linker), such as an acid labile phosphoramidate or a photolabile nitrobenzyl. In other embodiments, the distal end of the capture probe is tethered to a solid support via a selectively cleavable linker. Capture and washing of magnetic beads is performed post ligation to remove unligated terminal probe (as well as all other reaction components).

In some other embodiments, the reversible linker of the terminal probe is used as a second purification step to select the ligated target identifier from the unligated capture probe after cleaving from the magnetic beads. One example of a reversible linker is a polydeoxyAdenosine oligonucleotide of >20 bases. Using a second set of magnetic beads functionalized with polydeoxyThymidine oligonucleotides of >20 bases), the target identifiers are selectively captured, washed, and eluted into the electrolyte detection buffer as a highly purified and concentrated sample.

Figure 6:
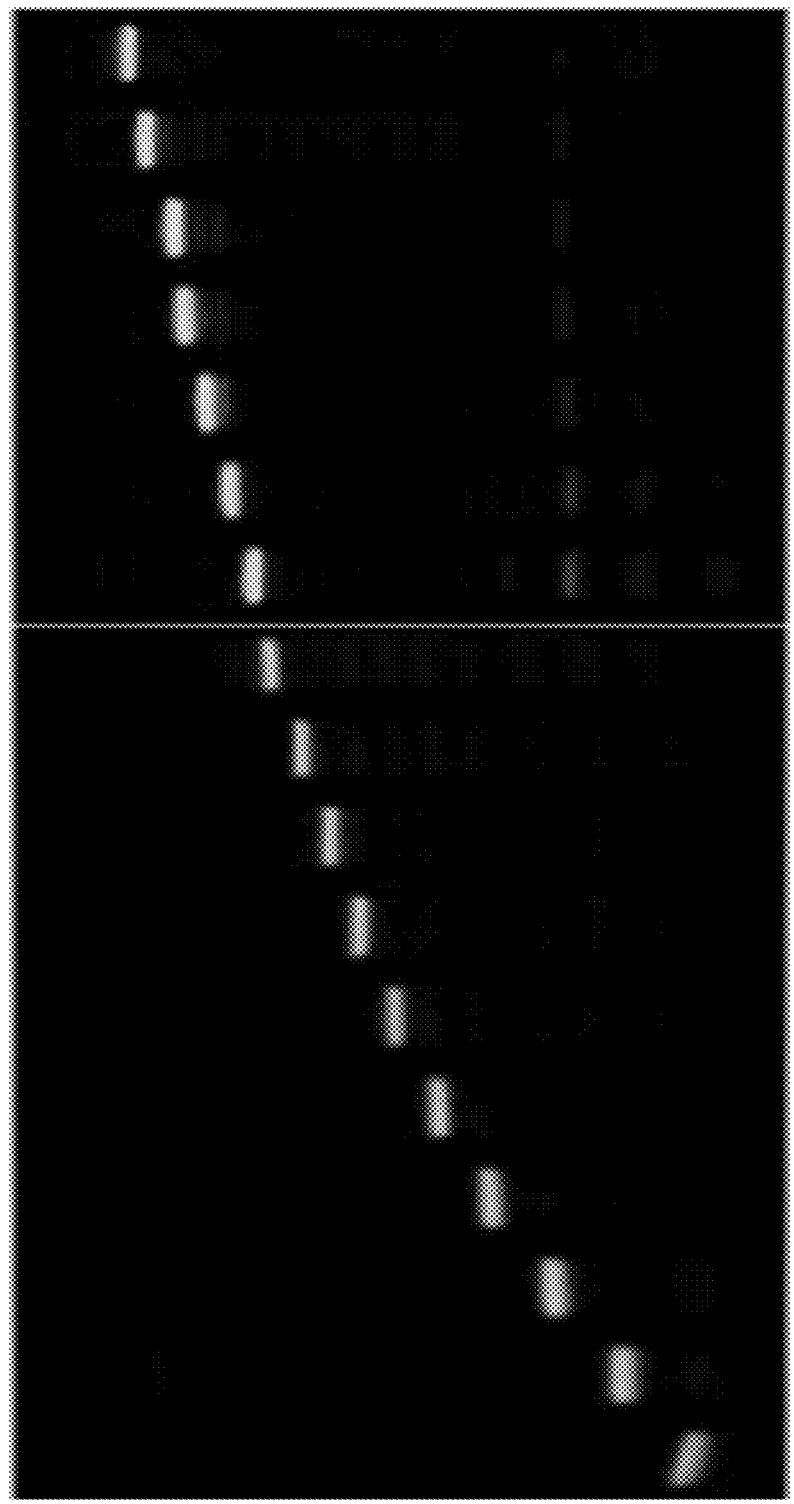
FIG. 6 is a gel from a competitive ligation assay that demonstrates specificity.

An important criterion of nucleic acid target identification is to minimize false positive readings. Ideally, a unique target template will produce target identifiers that form fully complementary basepairs with the target nucleic acid. By reducing the probability of mismatched basepairs and increasing the number of basepairs that are matched, the number of false positive measurements is reduced. Methods are used to promote such high fidelity detection. Capture probes are duplexed to the target templates below but near their thermal melt temperatures so as to destabilize duplexes with any mismatches. Ligase suppresses ligation of any oligomers having base mismatches with the template near the ligated nick (generally within 5 bases biased to the 3' side of the nick). Ligation under THL conditions increases this stringency, thus reducing ligation to probes with basepair mismatches. By using more than one ligation event to form the target identifier further increases the fidelity of the duplex matching by effectively increasing the number of basepairs that are positioned near a ligation. Using a full library of terminal probes (e.g., 256 4-base probes), or Xprobes as described below, reduces mismatches because when a correct match is preferentially ligated, it eliminates the opportunity for a mismatched probe to ligate. This is a competitive ligation which preferentially selects for the complementary probe. FIG. 6 shows high specificity when ligating base-modified probes using transient ligation in a competitive ligation with a library of sixteen base-modified 6-mer probes.

In particular, FIG. 6 is a gel electrophoresis image showing the results of 16 competitive THL reactions using a 96-base template. The template provides a single specific hybridization point for each of 16 different hexamer probes. Specificity of one of these constituent hexamers was tested in each of 16 THL reactions. For each reaction, 15 phosphorylated hexamer probes are used along with one non-phosphorylated hexamer probe. If ligated, the non-phosphorylated probe will terminate any further ligation. Thus, only non-specific ligation (of phosphorylated probes) will produce longer ligation products (than the terminated ligation product). In each of the 16 reaction lanes shown in FIG. 6, no measurable longer products were observed. This established a specificity bound >99% for this experimental setup.

Ligation blocking methods, such as unphosphorylated 5' probe termini demonstrated in the FIG. 6 reactions, are employed to reduce undesired side reaction products and to increase efficacy. 3' probe termini may also be blocked by conjugating it to a non-ligatable group (e.g., PEG or amine).

In general, the probe portions of both the capture probe and the terminal probe are blocked on the ends distal to the ligation site. During sample preparation, template termini may be blocked as well as any other 3' or 5' nucleic acid termini that are not participating in the preferred ligations.

The statistics of single molecule measurements provides a further technique in reducing false positives. Each target identifier measurement is independent and the identification of pathogens is through assessment of hundreds or thousands of measured target identifiers that provide a statistical basis for ignoring outliers and quantifying highly repeated reaction products.

In another embodiment, the method comprises identifying a target nucleic acid sequence in a sample by contacting the target nucleic acid sequence with a capture probe under conditions that provide for selective hybridization of the capture probe to a first portion of the target nucleic acid sequence, wherein the capture probe comprises a probe complementary to the first portion of the target nucleic acid sequence; ligating a first terminal probe to the capture probe under conditions that provide for transient hybridization of the first terminal probe to a second portion of the target nucleic acid sequence adjacent to the first portion of the target nucleic acid sequence, wherein the first terminal probe comprises a reporter tether and a probe complementary to the second portion of the target nucleic acid sequence; ligating a second terminal probe to the capture probe under conditions that provide for transient hybridization of the second terminal probe to a third portion of the target nucleic acid sequence located adjacent to the first portion of the target nucleic acid sequence, but at the opposite end of the probe of the capture probe from the second portion of target nucleic acid sequence, to form a target identifier, wherein the second terminal probe comprises a reporter tether and a probe complementary to the third portion of the target nucleic acid sequence; and detecting the target identifier and thereby identifying the target nucleic acid sequence in the sample.

The probe of the capture probe may comprise from 10 to 100 nucleobases. The capture probe may be tethered to a solid support by a linker (e.g., selectively cleavable linker), or comprises a linker (e.g., reversible linker) for tethering to a solid support.

The probe of the first and second terminal probes may comprise from 3 to 8 nucleobases. The first and second terminal probes may be tethered to a solid support by a linker (e.g., selectively cleavable linker), or comprises a linker (e.g., reversible linker) for tethering to a solid support. The reporter tether of the first and second terminal probes may comprise a reporter code that, upon detection, parses the genetic information of the second and third portion, respectively, of the target nucleic acid sequence to which the probe of the first and second terminal probes are complementary.

The target nucleic acid sequence may contact with a plurality of capture probes, wherein the probe of each capture probe is complementary to a different target nucleic acid sequence. The plurality of capture probes may be greater than 10, greater than 100, or greater than 1000.

The step of ligating the first and second terminal probes to the capture probe may comprise exposing the second and third portions of the target nucleic acid sequence to a plurality of terminal probes having probes with different combinations of nucleobases. The plurality of first and second terminal probes having probes with different combinations of nucleobases may be greater than 10, greater than 50, greater than 100, greater than 200, or greater than 1000.

The method may further comprise at least one step of capturing, washing and concentrating the target identifier prior to detection. The step of detecting may be accomplished by translocating the target identifier through a nanopore. The target identifier may be amplified prior to detection by, for example, polymerase chain reaction (PCR) or by thermal cycling.

Figure 7:
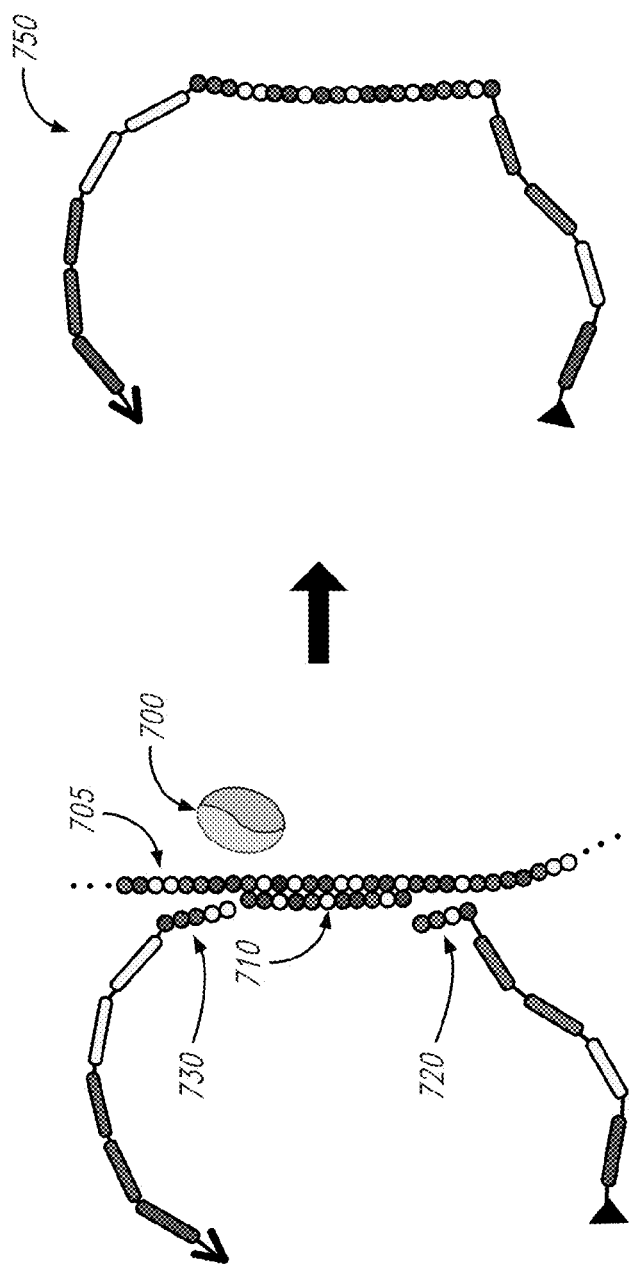
FIG. 7 shows an embodiment with a bidirectional THL extension of a capture probe.

FIG. 7 shows a single capture probe (710), having no reporter tether, hybridized to the target template (705). Each end of the capture probe is extended by THL utilizing ligase (700), with a 3' extending terminal probe (720) and a 5' extending terminal probe (730) to form a target identifier (750). The reporter code of the target identifier product is a concatenation of the two terminal probe reporter codes.

In some embodiments the capture probe is blocked on one end of the probe to limit ligation to a preferred direction. For example, the capture probe may have the phosphate removed on the 5' end to allow ligation only from its 3' terminus.

In another embodiment, the method comprises identifying a target nucleic acid sequence in a sample by contacting the target nucleic acid sequence with a capture probe under conditions that provide for selective hybridization of the capture probe to a first portion of the target nucleic acid sequence, wherein the capture probe comprises a reporter tether and a probe complementary to the first portion of the target nucleic acid sequence; ligating one or more nested probes to the capture probe under conditions that provide for transient hydridization of the one or more nested probes to a second portion of the target nucleic acid sequence adjacent to the first portion of the target nucleic acid sequence, wherein the one or more nested probes comprise probes complementary to the second portion of the target nucleic acid sequence, and wherein the one or more nested probes optionally comprise a reporter tether; ligating a terminal probe to the one or more nested probes under conditions that provide for transient hydridization of the terminal probe to a third portion of the target nucleic acid sequence adjacent to the second portion of the target nucleic acid sequence to form a target identifier, wherein the terminal probe comprises a reporter tether and a probe complementary to the third portion of the target nucleic acid sequence; and detecting the target identifier and thereby identifying the target nucleic acid sequence in the sample.

The probe of the capture probe may comprise from 10 to 100 nucleobases. The capture probe may be tethered to a solid support by a linker (e.g., selectively cleavable linker), or comprises a linker (e.g., reversible linker) for tethering to a solid support. The reporter tether of the capture probe comprises a reporter code that, upon detection, parses the genetic information of the first portion of the target nucleic acid sequence to which the probe of the capture probe is complementary.

The probes of the one or more nested probes may comprise from 3 to 8 nucleobases. The one or more nested probes may comprise a reporter tether. The reporter tether of the one or more nested probes may comprise a reporter code that, upon detection, parses the genetic information of the second portion of the target nucleic acid sequence to which the probes of the one or more nested probes are complementary. The reporter tether of the one or more nested probes may be in the form of a loop, and the method further comprises the step of opening the loop, prior to detection, to yield the reporter tether in linear form.

The probe of the terminal probe may comprise from 3 to 8 nucleobases. The terminal probe may be tethered to a solid support by a linker (e.g., selectively cleavable linker), or comprises a linker (e.g., reversible linker) for tethering to a solid support. The reporter tether of the terminal probe may comprise a reporter code that, upon detection, parses the genetic information of the third portion of the target nucleic acid sequence to which the probe of the terminal probe is complementary.

The target nucleic acid sequence may be contacted with a plurality of capture probes, wherein the probe of each capture probe is complementary to a different target nucleic acid sequence. The plurality of capture probes may be greater than 10, greater than 100, or greater than 1000.

The step of ligating the terminal probe to the one or more nested probes may comprise exposing the third portion of the target nucleic acid sequence to a plurality of terminal probes having probes with different combinations of nucleobases. The plurality of terminal probes having probes with different combinations of nucleobases may be greater than 10, greater than 50, greater than 100, greater than 200, or greater than 1000.

The method may further comprise at least one step of capturing, washing and concentrating the target identifier prior to detection. The step of detecting may be accomplished by translocating the target identifier through a nanopore. The target identifier may be amplified prior to detection by, for example, polymerase chain reaction (PCR) or by thermal cycling.

Figure 8:
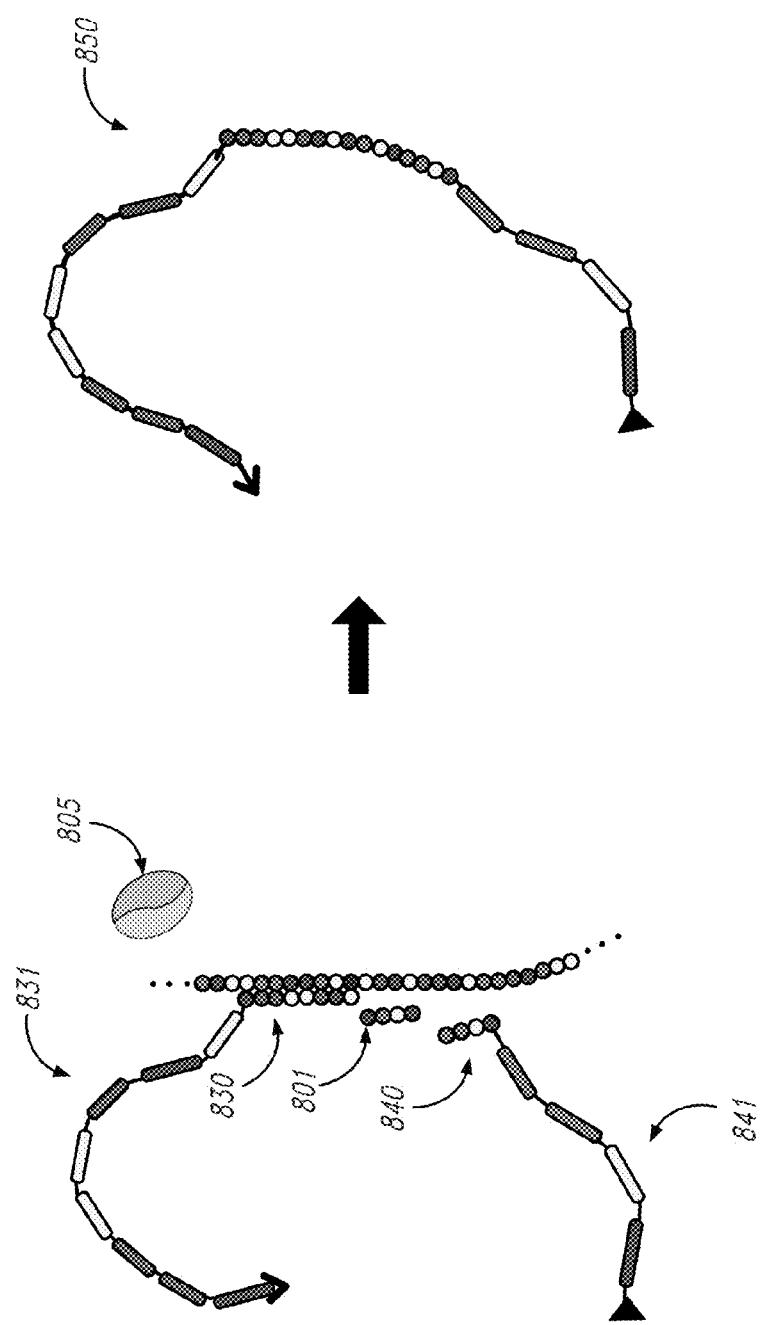
FIG. 8 shows an embodiment with a nested probe between the capture probe and the terminal probe.

One or more nested probes can be used to increase the specificity of the target identifier to improve nucleic acid target identification. In the embodiment shown in FIG. 8, the nested probe is a short probe with no reporter tether. The nested probe (801) is ligated via ligase (805) to a capture probe (830) having reporter tether (831), followed by ligation of the nested probe (801) to a terminal probe (840) having reporter tether (841). In some embodiments the nested probe may be ~3 to 8 bases long. By limiting the libraries of these simple nested probes and the corresponding terminal probes, only certain combinations of probes will be complementary to the target and extend the capture probes to produce the desired target identifier.

In another embodiment, the nested probes are Xprobes. Xprobes are used for nucleic acid sequencing methods collectively called sequencing by expansion (SBX) and disclosed in WO 2008/157696, WO 2009/055617 and PCT/US10/22654. In these embodiments, one or more Xprobes are sequentially ligated by THL to extend the capture probe. In some embodiments this capture probe extension may be ligated (by THL) to a terminal probe. A brief description of the Xprobe and its use in template dependant THL for SBX follows for clarity.

Figure 9:
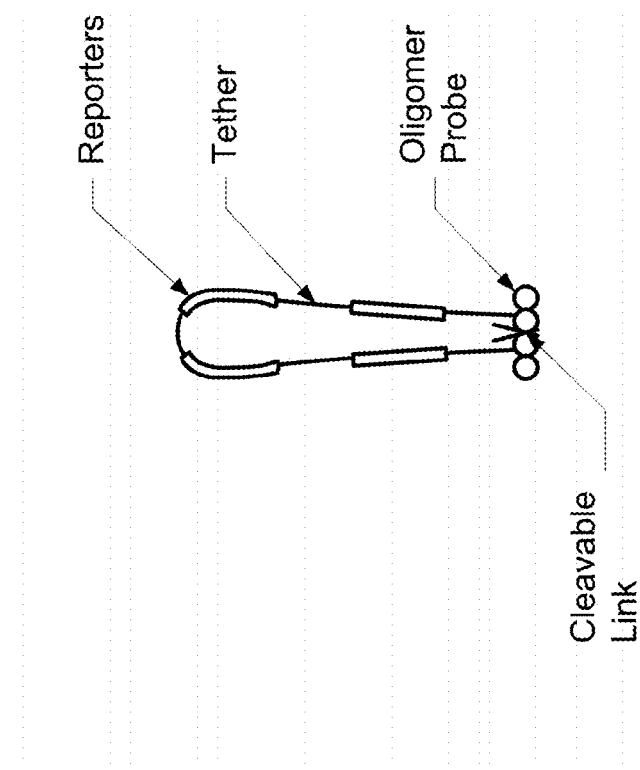
FIG. 9 is a representation of an SBX Xprobe.

One method of SBX uses building blocks called Xprobes (shown in FIG. 9), to specifically assemble, through enzymatic ligation, a spatially expanded representation of a target DNA sequence. This construct, called an Xpandomer, encodes sequences with high signal-to-noise reporters to enable high-throughput single-molecule DNA sequencing with multiple detection technologies (e.g., Coulter-based nanopore detection). An Xprobe has four structural elements; an oligomer probe, a looped tether, reporters on the tether that encode for the probe sequence, and a cleavable linker that is located between two probe-tether attachment points. If the linker is cleaved, the probe separates into two portions held together by a reporter tether.

Figure 10:
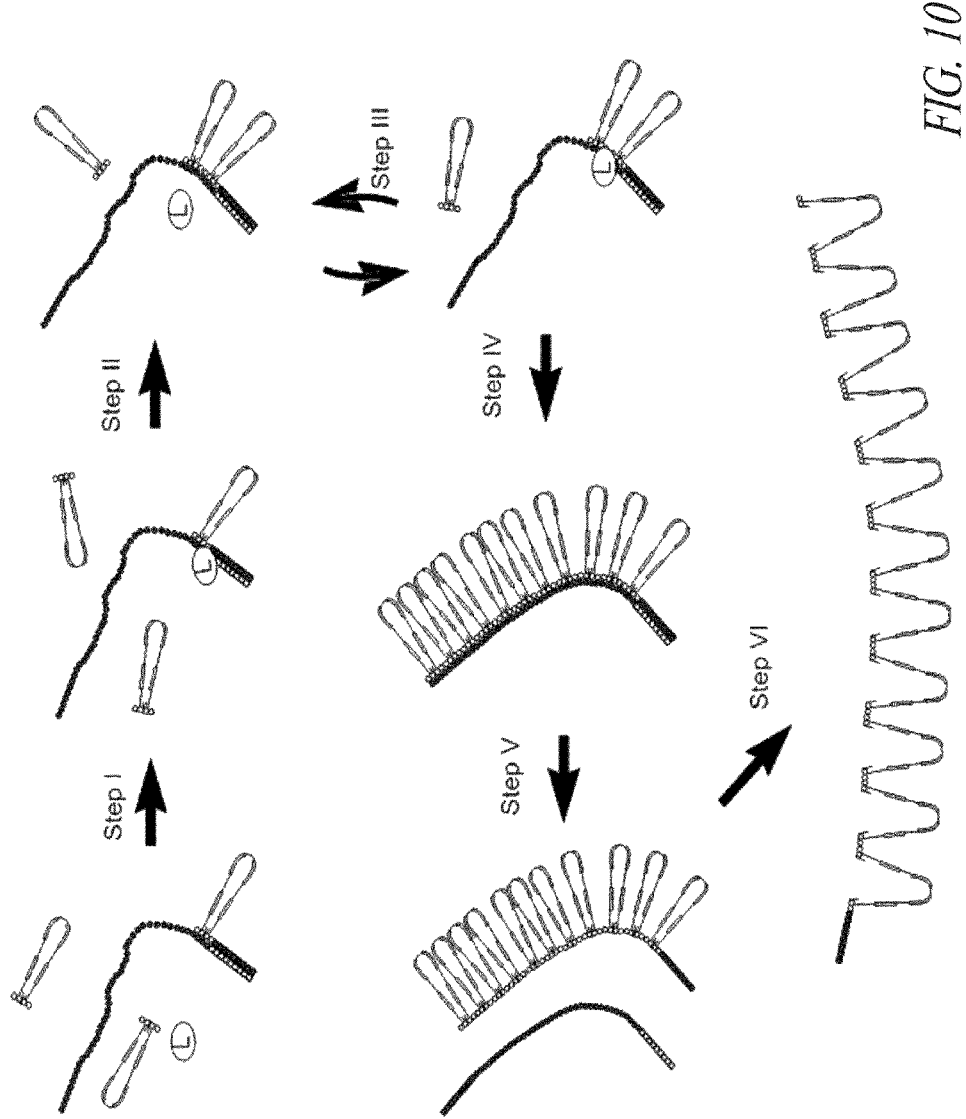
FIG. 10 is a schematic representation of a sequencing by expansion process that uses Xprobes.

FIG. 10 shows how Xprobes are used in a solution-based, template-dependant ligation process to serially link Xprobes into a product called an Xpandomer. The target identifier has similar characteristics to that of the expanded Xpandomer product. Before step I, DNA is fragmented and ligated with end adaptors to anneal to a sequencing primer and the primed template strand is contacted with a library of Xprobes and ligase (L). In Step I, conditions are adjusted to favor hybridization followed by ligation at a free 3'-OH of the primer template duplex. This is typically a THL reaction. In Steps II and III, the process of hybridization and ligation (typically THL) results in extension by cumulative addition of Xprobes extending from the primer end. These reactions occur in free solution and proceed until a sufficient amount of product has been synthesized. In Step IV, formation of a completed Xpandomer intermediate is shown. In Step V, the duplex is denatured and the Xpandomer is released. In the final step, the selectively cleavable links on the backbone are cleaved and allow the tether loops to "open up", forming the linearly elongated Xpandomer product.

To read Xpandomers in a nanopore detector, they are mixed with electrolyte and added to the nanopore input reservoir. The Xpandomers are electrophoretically drawn into the pore. As the reporters sequentially pass through the pore, they block the current by an amount corresponding to the reporter type. The sequence of blockages is then translated into sequence information. Thus by incorporating the SBX approach into the disclosed methods for identifying a target template, a target identifier having enriched information content can be obtained.

Figure 11:
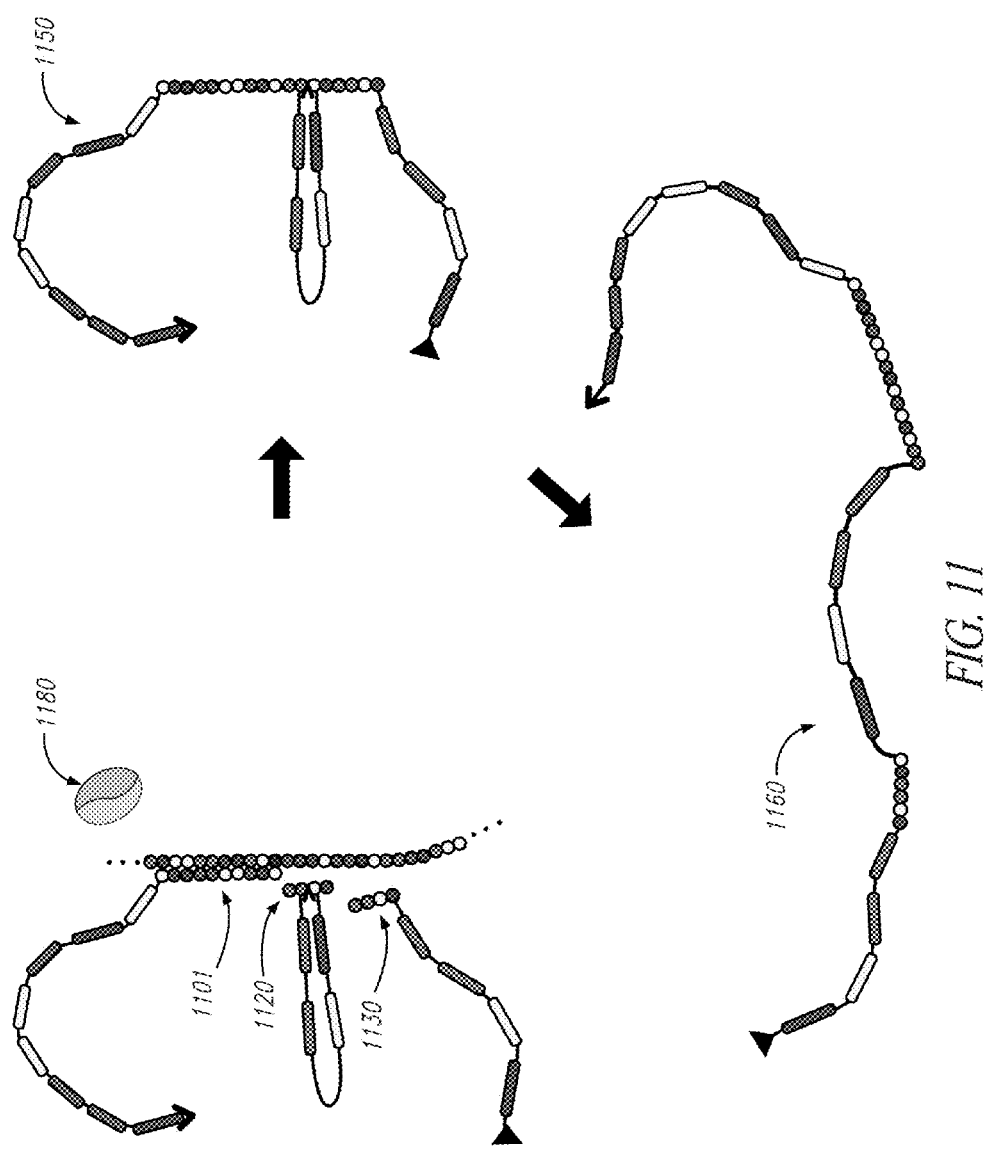
FIG. 11 shows an embodiment of a target identifier synthesis where an Xprobe is ligated between the capture probe and the terminal probe.

FIG. 11 depicts an embodiment where a capture probe (1101) is extended in either the 5' or 3' direction by THL utilizing ligase (1180) of a single Xprobe (1120) and a terminal probe (1130). The resulting product (1150) requires an additional cleavage step that opens the looped reporter tether to produce a target identifier having a linearized backbone (1160) so the reporters can be detected serially. A preferred embodiment uses full libraries of tetramer Xprobes and tetramer terminal probes that comprise all probe base combinations (256 combinations for each). Target identifier products have a capture probe at one end and a terminal probe at the other, but will have a variable number of Xprobes ligated between them. The number of nested Xprobes is a Poisson distribution that depends upon the relative concentrations of Xprobes to terminal probes. The lower the probability of incorporating a terminal probe with each extension ligation the more Xprobes are likely to be nested.

In another embodiment, the method comprises identifying a target nucleic acid sequence in a sample by contacting the target nucleic acid sequence with a first capture probe and a second capture probe under conditions that provide for selective hybridization of the first capture probe and the second capture probe to a first portion and a second portion, respectively, of the target nucleic acid sequence, wherein the first capture probe and the second capture probe comprise a reporter tether and a probe complementary to the first portion and the second portion, respectively, of the target nucleic acid sequence; ligating one or more nested probes to the first capture probe and the second capture probe under conditions that provide for transient hybridization of the one or more nested probes to a portion of the target nucleic acid sequence located between the first and second portions of the target nucleic acid sequence to form a target identifier, wherein the one or more nested probes comprise probes complementary to the nucleic acid sequence located between the first and second portions of the target nucleic acid sequence, and wherein the one or more nested probes optionally comprise a reporter tether; and detecting the target identifier and thereby identifying the target nucleic acid sequence in the sample.

The probes of the first capture probe and second capture probe may comprise from 10 to 100 nucleobases. The first capture probe and second capture probe may be tethered to a solid support by a linker (e.g., selectively cleavable linker), or comprises a linker (e.g., reversible linker) for tethering to a solid support. The reporter tether of the first capture probe and second capture probe may comprise a reporter code that, upon detection, parses the genetic information of the first portion and the second portion, respectively, of the target nucleic acid sequence to which the probe of the first capture probe and probe of the second capture probe are complementary.

The probes of the one or more nested probes may comprise from 3 to 8 nucleobases. The one or more nested probes may comprise a reporter tether. The reporter tether of the one or more nested probes may comprise a reporter code that, upon detection, parses the genetic information of the portion of the target nucleic acid sequence located between the first and second portions of the target nucleic acid sequence to which the probes of the one or more nested probes are complementary. The reporter tether of the one or more nested probes may be in the form of a loop, and the method further comprises the step of opening the loop, prior to detection, to yield the reporter tether in linear form.

The target nucleic acid sequence may be contacted with a plurality of the first and second capture probes, wherein the probe of each of the plurality of first and second capture probe is complementary to a different target nucleic acid sequence. The plurality of the first and second capture probes may be greater than 10, greater than 100, or greater than 1000.

Figure 12:
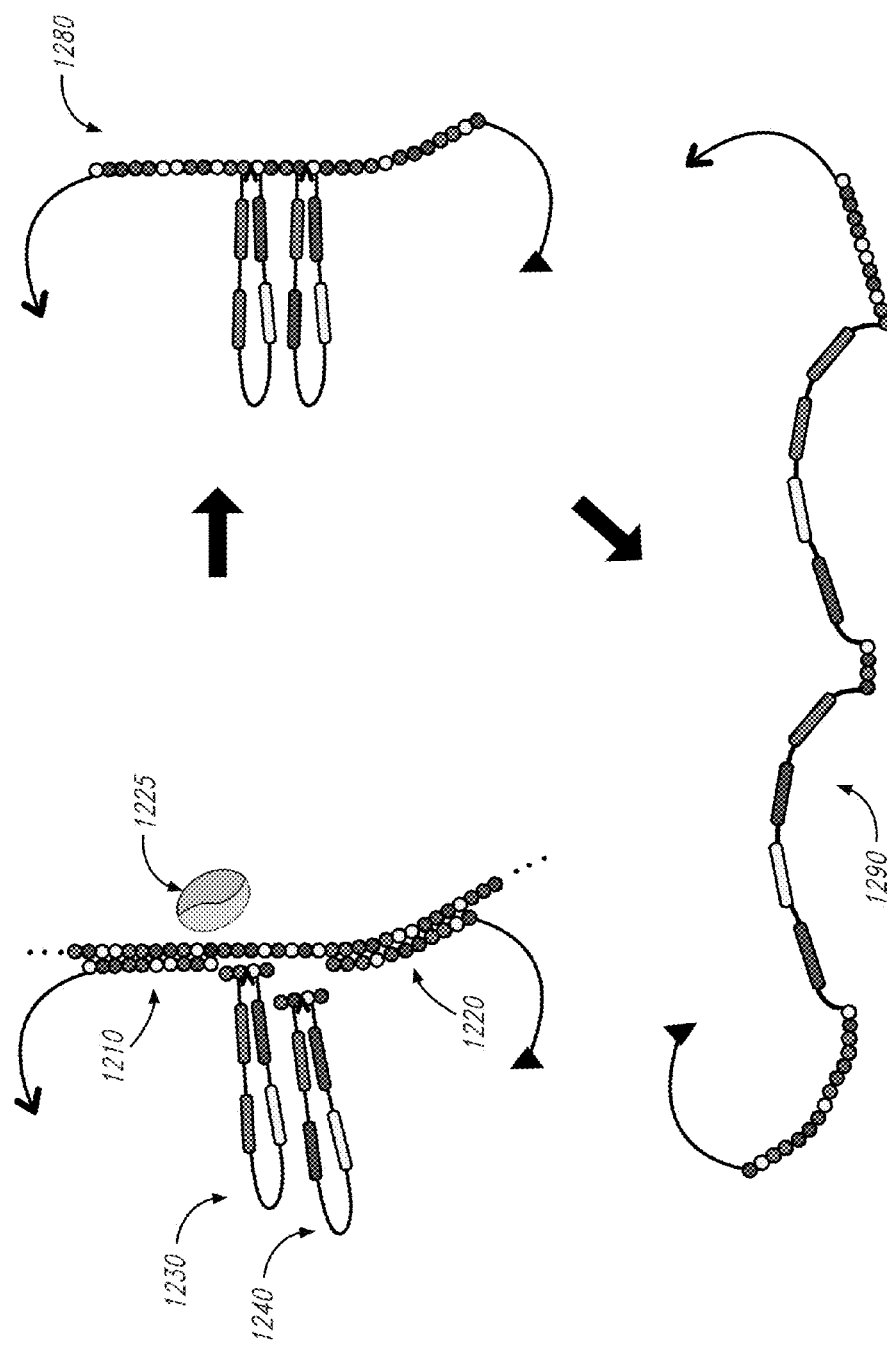
FIG. 12 shows an embodiment of a target identifier synthesis where two Xprobes are ligated between two capture probes.

FIG. 12 depicts an embodiment that uses two capture probes that have tethers with T-linkers, but no reporters (1210, 1220). In this embodiment, the capture probes are hybridized to two complementary portions of the target template between which an 8-base gap forms. Two 4-base Xprobes (1230, 1240) transiently hybridize in the gap and link to the capture probes and to each other by THL with ligase (1225) to form a target identifier (1280) specific to the target template. As with other embodiments with Xprobes, a cleavage step is then employed to open the two looped reporter tethers and produce a target identifier sequence of reporters along a linearized backbone (1290). In other embodiments, target identifiers can be formed with >2 Xprobes by filling gaps with corresponding number of bases. One embodiment uses a full Xprobe library of 256 tetramer probe base combinations.

Tethers are generally resistant to entanglement or are folded so as to be compact. Polyethylene glycol (PEG), polyethylene oxide (PEO), methoxypolyethylene glycol (mPEG), and a wide variety of similarly constructed PEG derivatives (PEGs) are broadly available polymers that can be utilized in the practice of this invention. Modified PEGs are available with a variety of bifunctional and heterobifunctional end crosslinkers and are synthesized in a broad range of lengths. PEGs are generally soluble in water, methanol, benzene, dichloromethane, and many common organic solvents. PEGs are generally flexible polymers that typically do not non-specifically interact with biological chemicals.

Other polymers that may be employed as tethers, and provide "scaffolding" for reporters, include, for example, polyglycine, poly-proline, poly-hydroxyproline, poly-cysteine, poly-serine, poly-aspartic acid, poly-glutamic acid, and the like. Side chain functionalities can be used to build functional group-rich scaffolds for added signal capacity or complexity.

T-linkers are typically on the distal end of the reporter tethers of capture probes and terminal probes. A T-linker is generally coupled with a T-linker receptor to complete the linkage to the solid substrate (e.g. bead). In some cases the T-linker is cleaved (to uncouple from the solid substrate) leaving T-linker residues on the product ends. A T-linker is used for purifying and concentrating target identifiers and includes selectively cleavable linkers and selectively linkable linkers. Selectively cleavable linkers are described below. Selectively linkable linkers include a variety of covalent chemical linkers, biological linker pairs and combinations thereof. A preferred T-linker is an oligomer (10 to 50 bases) that will selectively hybridize (couple) to its complementary oligomer (T-linker receptor).

In some embodiments, the selectively cleavable linker may be a covalent bond. A broad range of suitable commercially available chemistries (Pierce, Thermo Fisher Scientific, USA) can be adapted for preparation of the probes comprising selectively cleavable linker bonds. Common linker chemistries include, for example, NHS-esters with amines, maleimides with sulfhydryls, imidoesters with amines, EDC with carboxyls for reactions with amines, pyridyl disulfides with sulfhydryls, and the like. Other embodiments involve the use of functional groups like hydrazide (HZ) and 4-formylbenzoate (4FB) which can then be further reacted to form linkages. More specifically, a wide range of crosslinkers (hetero- and homo-bifunctional) are broadly available (Pierce) which include, but are not limited to, Sulfo-SMCC (Sulfosuccinimidyl 4-[N-maleimidomethyl]cyclohexane-1-carboxylate), SIA (N-Succinimidyl iodoacetate), Sulfo-EMCS ([N-e-Maleimidocaproyloxy]sulfosuccinimide ester), Sulfo-GMBS (N-[g-Maleimido butyryloxy]sulfosuccinimide ester), AMAS N-(a-Maleimidoacetoxy)succinimide ester), BMPS(N EMCA (N-e-Maleimidocaproic acid)-[β-Maleimidopropyloxy]succinimide ester), EDC (1-Ethyl-3-[3-dimethylaminopropyl]carbodiimide Hydrochloride), SANPAH (N-Succinimidyl-6-[4"-azido-2"-nitrophenylamino]hexanoate), SADP (N-Succinimidyl(4-azidophenyl)-1,3"-dithiopropionate), PMPI (N-[p-Maleimidophenyl]isocy, BMPH (N-[β-Maleimidopropionic acid]hydrazide, trifluoroacetic acid salt)anate), EMCH ([N-e-Maleimidocaproic acid] hydrazide, trifluoroacetic acid salt), SANH (succinimidyl 4-hydrazinonicotinate acetone hydrazone), SHTH (succinimidyl 4-hydrazidoterephthalate hydrochloride), and C6-SFB (C6-succinimidyl 4-formylbenzoate). Also, the method disclosed by Letsinger et al. ("Phosphorothioate oligonucleotides having modified internucleoside linkages", U.S. Pat. No. 6,242,589) can be adapted to form phosphorothiolate linkages.

Further, well-established protection/deprotection chemistries are broadly available for common linker moieties (Benoiton, "Chemistry of Peptide Synthesis", CRC Press, 2005). Amino protection include, but are not limited to, 9-Fluorenylmethyl carbamate (Fmoc-NRR'), t-Butyl carbamate (Boc-NRR'), Benzyl carbamate (Z—NRR', Cbz-NRR'), Acetamide Trifluoroacetamide, Phthalimide, Benzylamine (Bn-NRR'), Triphenylmethylamine (Tr-NRR'), and Benzylideneamine p-Toluenesulfonamide (Ts-NRR'). Carboxyl protection include, but are not limited to, Methyl ester, t-Butyl ester, Benzyl ester, S-t-Butyl ester, and 2-Alkyl-1,3-oxazoline. Carbonyl include, but are not limited to, Dimethyl acetal 1,3-Dioxane, and 1,3-Dithiane N,N-Dimethylhydrazone. Hydroxyl protection include, but are not limited to, Methoxymethyl ether (MOM-OR), Tetrahydropyranyl ether (THP-OR), t-Butyl ether, Allyl ether, Benzyl ether (Bn-OR), t-Butyldimethylsilyl ether (TBDMS-OR), t-Butyldiphenylsilyl ether (TBDPS-OR), Acetic acid ester, Pivalic acid ester, and Benzoic acid ester.

EXAMPLES

Example 1

Identification of a Target Sequence within a Mixed Nucleic Acid Sample

Oligonucleotide sequences complementary to the capture probe and terminal probe portions of a target template are prepared by automated DNA synthesis. A reporter tether linked via a selectively cleavable bond to a magnetic bead is linked to the oligonucleotide complementary to the capture probe portion of the target template. Similarly a terminal probe is prepared by linking a reporter tether comprising the terminal probe reporter code and a polydeoxyAdenosine moiety to the oligonucleotide complementary to the terminal probe portion of the target template.

The capture probe and terminal probe are admixed with a sample comprising ligase enzyme and a target nucleic acid having a target template. After sufficient time for ligation, the magnetic beads are isolated and washed. The selectively cleavable linker is then cleaved and the magnetic beads removed by filtration. To the filtrate is added a polydeoxyThymidine moiety which is chemically linked to a magnetic bead. After sufficient time for hybridization of the polydeoxyAdenosine moiety with the polydeoxyThymidine moiety, the mixture is filtered and the magnetic beads isolated. The purified target identifier is then isolated by denaturing the polydeoxyAdenosine/polydeoxyThymidine duplex and filtering off the magnetic beads.

The isolated target identifier is presented to the nanopore detector as a concentrated solution. The reporter code is parsed and the genetic sequence of the target template is determined. The source of the target nucleic acid (e.g., a pathogen) is then determined from the genetic sequence of the target template.

Example 2

Synthesis and Purification of Target Identifier

Figure 13:
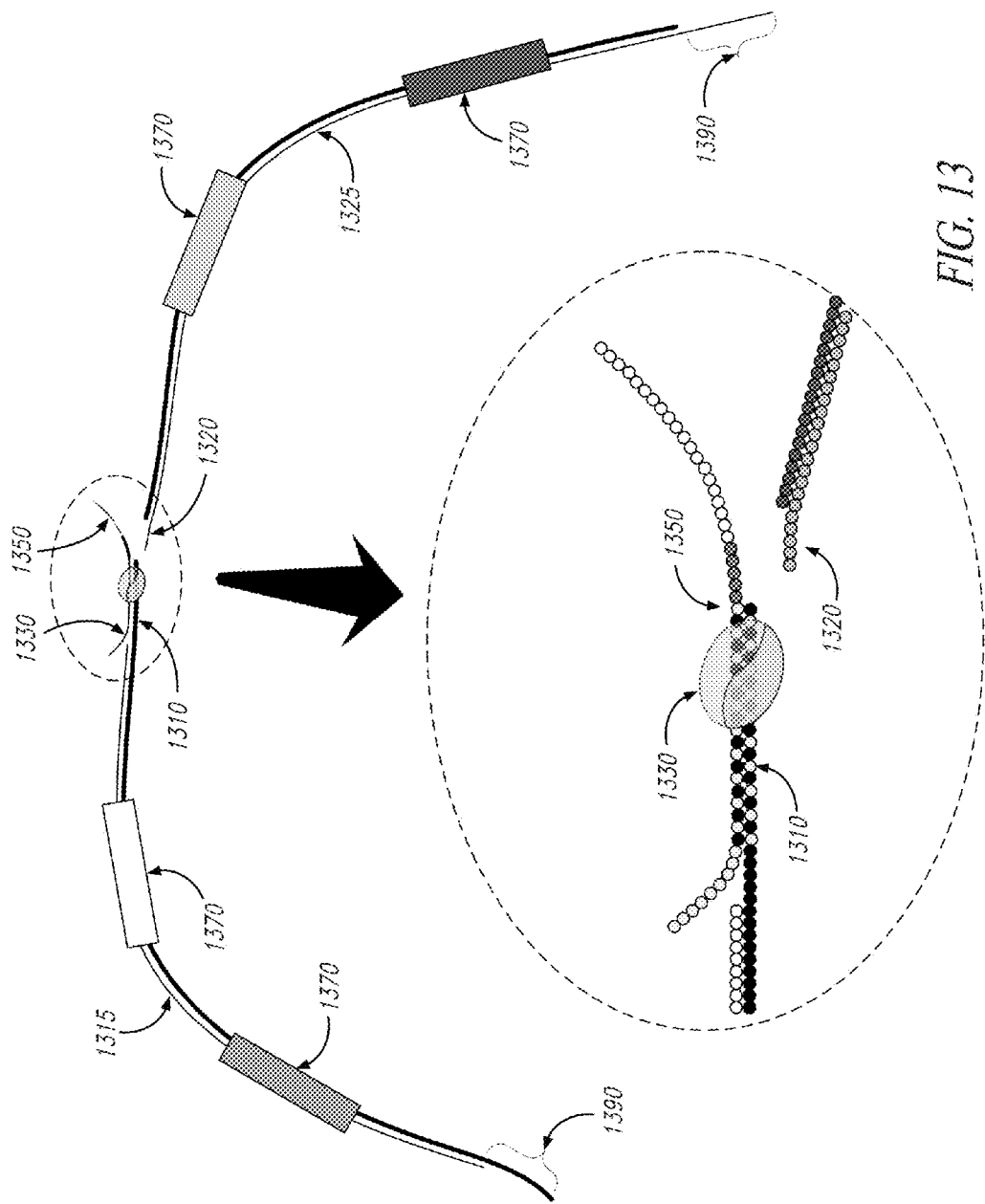
FIG. 13 is a schematic showing ligation of the capture probe and the terminal probe, each with oligonucleotide T-linkers, in the presence of the target template to form the target identifier.

Referring to FIG. 13, to demonstrate the specificity and efficiency of transient hybridization ligation for one embodiment, capture probe (1310) and terminal probe (1320) specific to template (1350) were ligated with ligase (1330) using an on-bead assay to produce a target identifier. Capture probe (1310) and terminal probe (1320) have reporter tethers (1315, 1325, respectively), with the reporter tethers having reporters (1370) and T-linker (1390). Efficient purification of the target identifier was demonstrated using magnetic beads functionalized with oligonucleotides that are complementary to T-Linker affinity handles.

Figure 14:
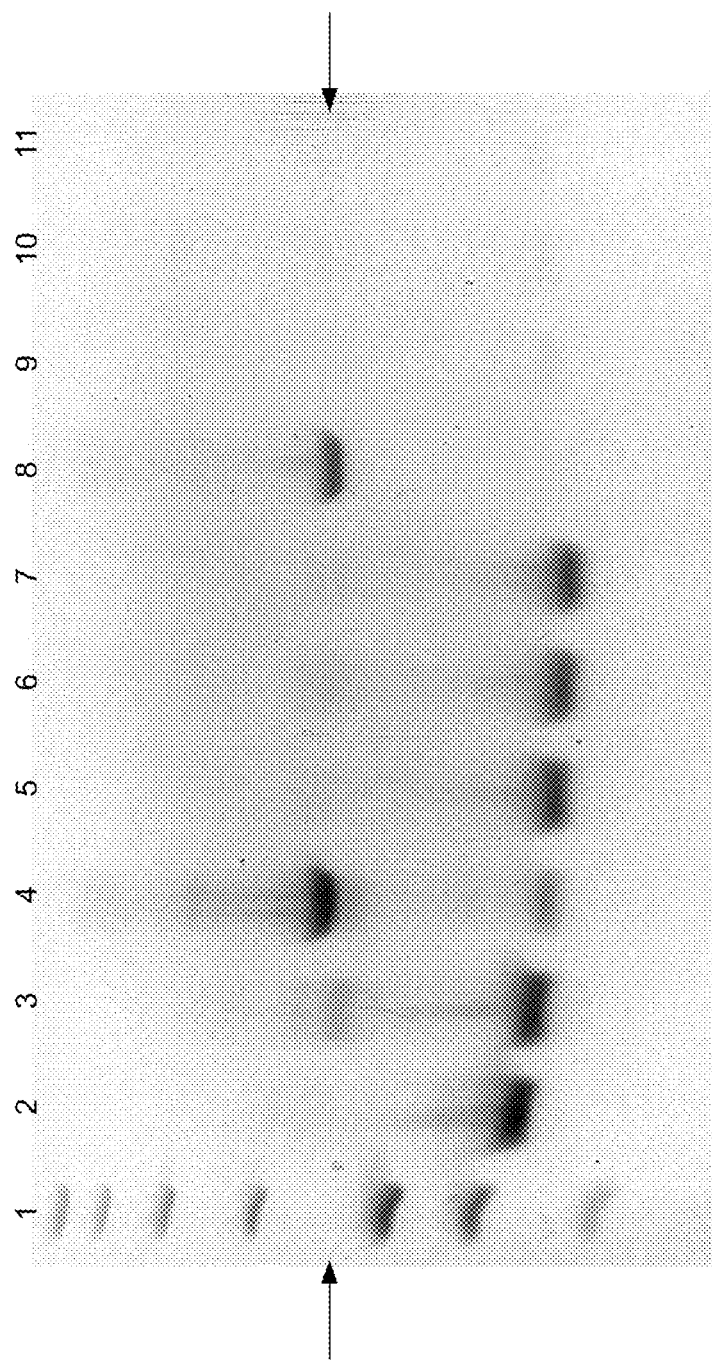
FIG. 14 is a gel image that demonstrates the specificity of transient hybridization ligation for Target Identifier synthesis along with the efficiency of oligonucleotide T-linker purification for one embodiment of the invention.

Target identifier and unligated probes were analyzed by agarose gel electrophoresis (E-gel, 1.2% with SYBR Safe; Invitrogen Corporation; Carlsbad, Calif.). The 11-lane gel image is shown in FIG. 14. The capture probe (lane 2), which has a 25-base 5' phosphorylated overhang and a 3' oligonucleotide deoxyadenosine affinity handle distal to the ligation overhang, was simultaneously hybridized to oligonucleotide deoxythymidine (25-mer) functionalized magnetic beads (Dynabeads Oligo (dT)25; Invitrogen Corporation; Carlsbad, Calif.) and each of four templates: (1) Template_0_0 (lanes 4 and 8) was fully complementary to both the capture probe and terminal probe overhangs; (2) Template_0_1 (lanes 5 and 9) had a single mismatch (A-A) at the final nucleotide of the terminal probe 3' overhang; (3) Template_1_0 (lanes 6 and 10) had a single mismatch (G-G) at the final nucleotide of the capture probe 5' overhang; and (4) Template_1_1 (lanes 7 and 11) had a single mismatch at the final nucleotide of both the terminal probe 3' overhang (A-A) and the capture probe 5' overhang (G-G).

Capture probe, target template, and Oligo-dT magnetic beads were admixed in 1×T4 DNA Ligase Buffer (Epicentre Biotechnologies, Madison, Wis.) and allowed to hybridize. Mixture was cooled slowly to 23° C. and magnetic beads were captured and washed to remove excess template. Beads with capture probe/target template duplex were resuspended in ligation reaction mix and spiked with terminal probe comprising a 5-base, 3' overhang, a reporter tether, and a T-linker affinity handle distal to the ligation overhang. Terminal probe size reference is run in lane 3 (FIG. 14). Reaction mixes were heated to 37° C., spiked with T4 DNA ligase (T4 DNA Ligase (Rapid); Enzymatics; Beverly, Mass.) and incubated 60 minutes at 37° C. Sample included salts, buffer, and ATP as appropriate to support ligation. Magnetic beads were washed three times with 6 to 7 volumes of a bead binding solution of 500 mM NaCl, 10 mM Tris Buffer, 20 mM EDTA and 1% N-lauroylsarcosine, and two times with 7 volumes of a wash solution of 500 mM NaCl, 10 mM Tris Buffer and 20 mM EDTA, to remove excess terminal prove and ligation reaction mix. Beads were resuspended with water and product was eluted from the Oligo-dT beads (lanes 4-7) by heating to 50° C.

Following this purification, and as shown in FIG. 14, the fully matched template (lane 4) facilitated ≥90% dimerization, while all three mismatched templates (lanes 5-7) allowed for very little ligation. These results demonstrate high specificity at a temperature significantly higher than the melting temperature of the terminal probe overhang.

Reactions were subsequently purified using magnetic beads functionalized with a capture oligonucleotide (5' AACGCACTCAATCCATCTTCAGGT 3'; 3' bead linkage) complementary to the affinity handle on the terminal probe T-linker (5' ACCTGAAGATGGATTGAGTGCGTT 3') to remove unligated capture probe (lanes 8-11). Following this purification, the mismatched template reactions (lanes 9-11) have almost no remaining monomer or dimer, while the fully matched template reaction (lane 8) is almost entirely in dimer form, confirming that the ligation was complete and the dimer can be double bead-purified using T-linker affinity handles. Lane 1 is a molecular ladder that provides size reference confirmation of probes and ligation products, and the full-length product is shown by arrows.

Example 3

Purification Using Oligonucleotide T-Linkers

Figure 15:
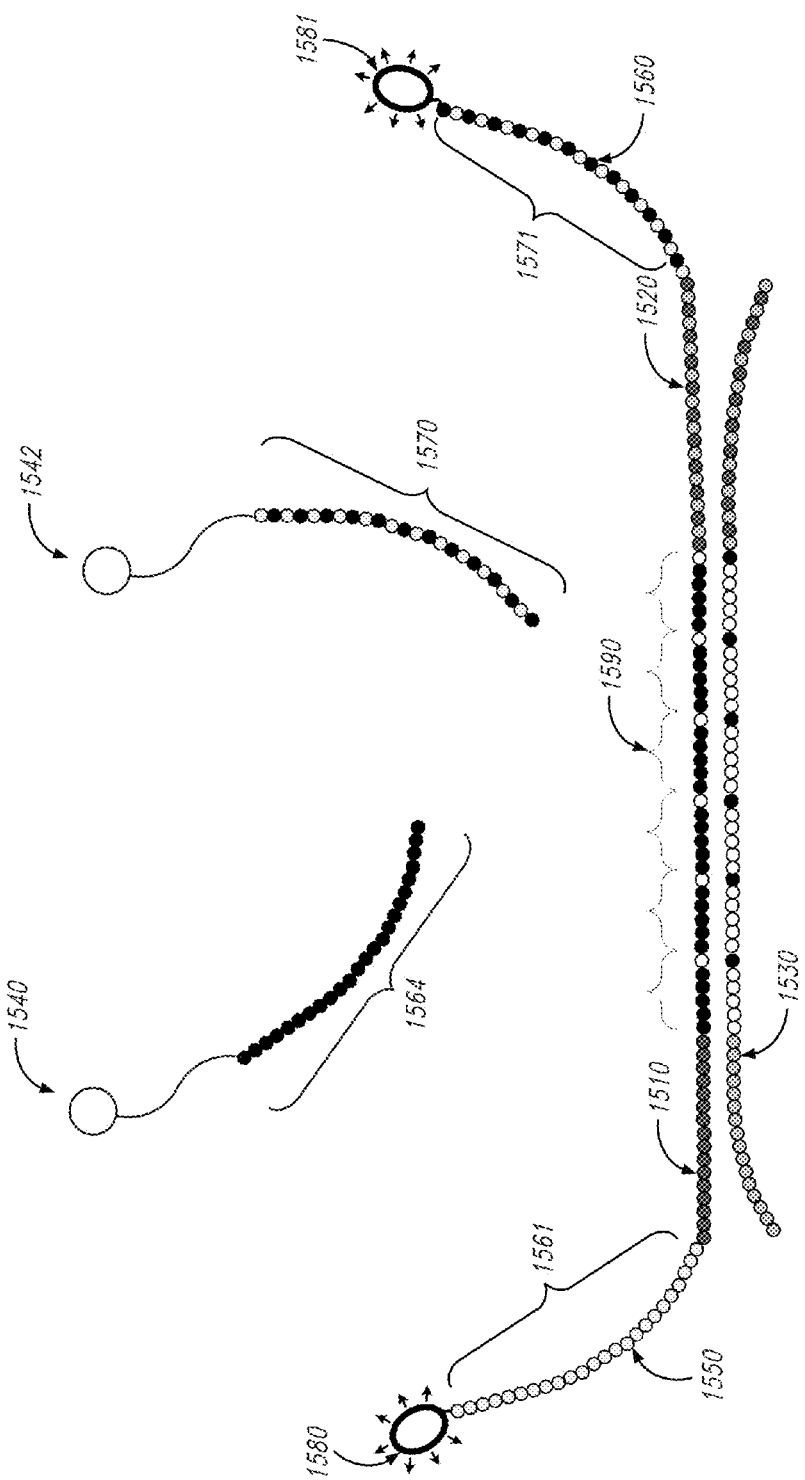
FIG. 15 is a schematic that describes a test case for purification of fluorescently labeled ligation product using oligonucleotide T-linkers.

To demonstrate the utility of T-linkers for target identifier purification, full-length ligation products were synthesized containing two distinct oligonucleotide T-linker moieties, one on the 5' end and the other on the 3' end of the construct as illustrated in FIG. 15. In particular, capture probes (1510, 1520) were selectively hybridized to template (1530). Capture probes (1510,1520) contained a reporter tether (1550, 1560), the terminal portion of which (distal to the ligation end) were fluorescently labeled with a fluorophore (1580, 1581) (NHS-Rhodamine; Thermo Scientific; Rockford, Ill.) to permit detection. The gap between the two capture probes was filled using template-dependent ligation (T4 DNA Ligase, Enzymatics Inc., Beverly, Mass.) to insert six basic hexamer probes (1590).

In addition to the full-length ligation product with T-linker affinity handles on each end, a range of fluorescently labeled truncation products were produced during the ligation synthesis reaction. Since none of the truncation products contain both T-linker handles, sequential purification of this test sample using magnetic beads (functionalized with oligonucleotides complementary to the T-linkers) should yield only the full-length ligation product.

Oligonucleotide deoxythymidine (25-mer) functionalized magnetic beads (1540) (Dynabeads Oligo (dT)25; Invitrogen Corporation; Carlsbad, Calif.) were used for the first bead purification step to specifically capture the oligonucleotide deoxyAdenosine affinity handle on the first T-linker. Briefly, the sample was heated to 95° C. for 20 seconds in the presence of magnetic beads (1540) and 1 volume of a bead binding solution (BBTS) of 500 mM NaCl, 20 mM Tris Buffer, 10 mM EDTA, 1% N-lauroylsarcosine, and 1% Tween 20. Sample was continually mixed while cooling to room temperature, allowing the Poly A tail (1561) of the first T-linker to specifically hybridize to the Oligo(dT)25 tethered to the magnetic beads (1564). The sample was then washed with BBTS solution to remove non-specifically bound ligation product. Purified sample is recovered by heat denaturation (of the Poly dA/dT duplex), bead capture, and removal of the aqueous fraction. The second bead purification protocol follows the same basic process, but using magnetic beads (1542) functionalized with a capture oligonucleotide (5' AACGCACTCAATCCATCTTCAGGT 3'; 3' bead linkage) (1570) complementary to the affinity handle on the second T-linker (5' ACCTGAAGATGGATTGAGTGCGTT 3') (1571).

Figure 16:
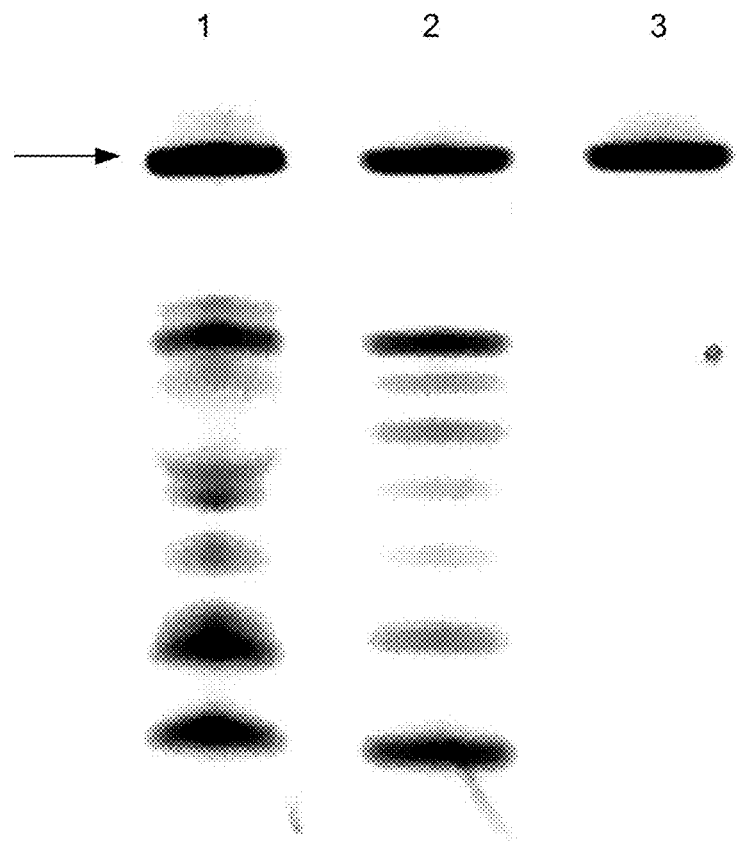
FIG. 16 is a gel image that demonstrates high efficiency purification of full-length ligation product using two distinct oligonucleotide T-linker moieties, one on the 5' end and the other on the 3' end of the construct.

FIG. 16 shows the gel electrophoresis image with 3 lanes: Lane 1 shows the reaction products prior to purification; Lane 2 shows the reaction products after the $1^{st}$ purification (using the $1^{st}$ T-linker); and Lane 3 shows the reaction products after the $2^{nd}$ purification (using the $2^{nd}$ T-linker) wherein all truncated ligation products were eliminated leaving only a single band of the targeted double T-linker ligation product. The full-length product is shown in FIG. 16 by the arrow.

Example 4

Enhanced Target Sequence Detection Using Thermal Cycling

Referring to FIG. 17A, capture probe (1710) and terminal probe (1720) are admixed with a sample comprising thermostable DNA ligase enzyme (1730) and a target nucleic acid having a target template (1740). Sample includes salts, buffer, and cofactors such as ATP or NAD as appropriate to support ligation. Both probes are synthesized with multiple 4-state reporters (1725) along their reporter tethers (1760) to provide unique reporter codes. Each probe type has a distinct oligonucleotide T-linker (1762). Capture probe (1710) is depicted as a 15-base probe moiety, while the terminal probe (1720) is depicted as a hexamer probe moiety.

In FIG. 17A, capture probe (1710) is shown hybridizing to template (1740), while FIG. 17B depicts the THL of terminal probe (1720) to template (1740), both steps being performed at 37° C. As shown in FIG. 17C, the temperature is raised and the resulting target identifier (1780) is released from template (1740), beginning a new cycle at depicted in Figure A. This thermal cycling is repeated, thus amplifying the number of target identifiers produced in the ligation reaction.

Example 5

Amplification of Target Identifier Using Polymerase

Figure 18A:
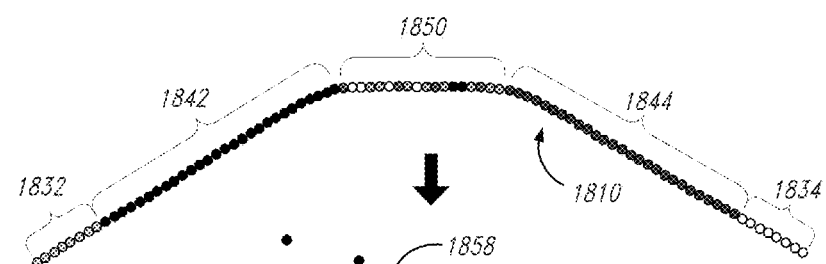
FIG. 18 is a schematic showing aspects of a method for target identifier amplification using polymerase; specifically, (a) a target identifier, (b) hybridization of the target identifier to a magnetic bead via a second T-linker, (c) an amplified reverse complement of the target identifier, and (d) the free target identifier complement.
Figure 18B:
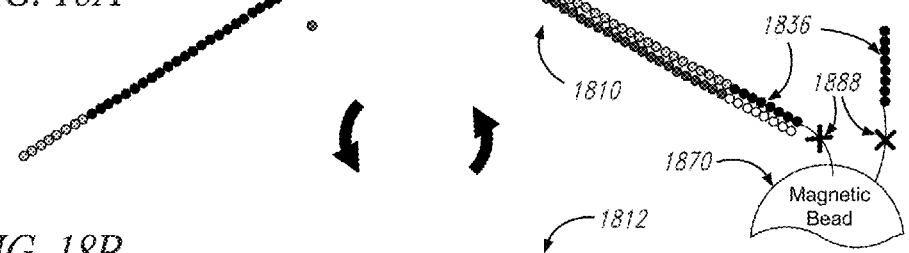
Figure 18C:
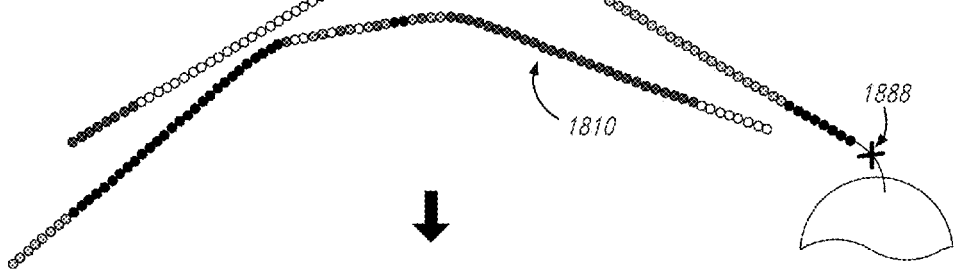
Figure 18D:
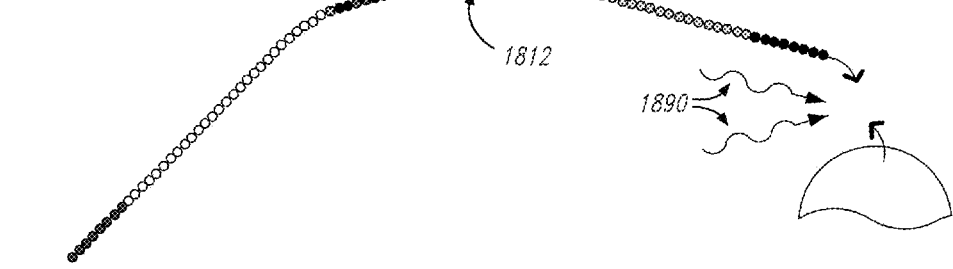

Referring to FIG. 18A, target identifier (1810) has a contiguous single-stranded nucleic acid which include first and second T-linkers (1832,1834), coded reporter tethers (1842, 1844), and target specific probes (1850) derived from both the capture probe and terminal probe. As shown in FIG. 18B, target identifier (1810) is hybridized to magnetic bead (1870) via the second T-linker (1834). The receptor (1836) for the second T-linker (1834) is an oligonucleotide that duplexes with the 3' terminus of the target identifier such that the 3' end of the receptor is extendable by polymerase (1858). The second T-linker also comprises a selectively cleavable photo-labile linker (1888). After washing beads to remove any remaining truncated product, sample is resuspended with a reaction mix that includes salts, buffer, and dNTP's to support polymerase extension. Pfu high fidelity DNA polymerase (Promega, Madison, Wis.) is added and the sample is thermal cycled between 95° C., 50° C., and 72° C. to enable repeated denaturation, annealing, and polymerase extension (represented by the circular arrows of FIG. 18), thus providing an amplified reverse complement (1812) of target identifier (1810) as shown in FIG. 18C. Following linear amplification, beads are thoroughly washed to eliminate all but the bead-bound target identifier complement. Beads are exposed to 365 nm UV source (1890) to selectively cleave photolabile linker (1888), yielding the free target identifier complement (1812) as shown in FIG. 18D.

Example 6

Detection of Target Identifier in a Solid-State Nanopore

Figure 19:
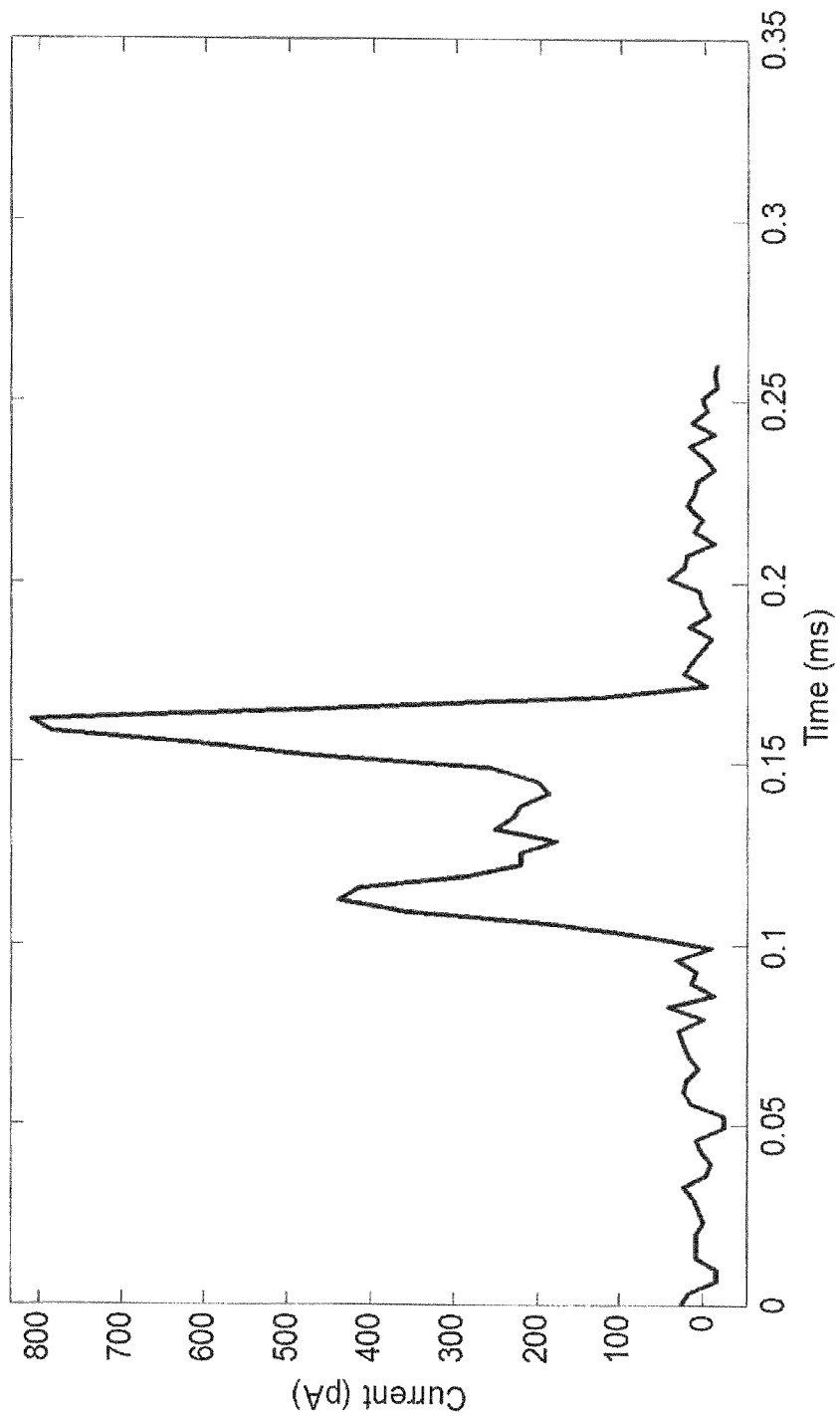
FIG. 19 is a time trace of the current measurement associated with a 2-peak, 2-state target identifier passing through a solid-state nanopore.

FIG. 19 is a time trace that records the current measurement caused by a 2-peak, 2-state target identifier passing through a solid-state nanopore. This was recorded with a 100 kHz bandwidth filter on an Axopatch 200B amplifier, and demonstrates reporter resolution<25 us/reporter. The target identifier was assembled via THL in the manner described in Example 2 above. The tethers of the capture and terminal probes each had a ds-DNA backbone with a single reporter of 210 bases that have short side-chain oligomers attached at every 10 bases. For both the capture and terminal probes, the reporter moiety was positioned 200 bases from the ligation site and 200 bases from the T-linker. The capture probe and terminal probe reporters had side-chain lengths of 10 and 20 bases, respectively, that result in the two peak heights as shown in FIG. 19.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

The invention claimed is:

1. A method for identifying a target nucleic acid sequence in a sample, the method comprising:
   contacting the target nucleic acid sequence with a capture probe under conditions that provide for selective hybridization of the capture probe to a first portion of the target nucleic acid sequence, wherein the capture probe comprises a reporter tether and a probe complementary to the first portion of the target nucleic acid sequence;
   ligating one or more nested probes to the capture probe under conditions that provide for transient hybridization of the one or more nested probes to a second portion of the target nucleic acid sequence adjacent to the first portion of the target nucleic acid sequence, wherein the one or more nested probes comprise probes complementary to the second portion of the target nucleic acid sequence, and wherein the one or more nested probes optionally comprise a reporter tether, provided that at least one of the one or more nested probes comprise a reporter tether in the form of a loop, and further comprising the step of opening the loop, prior to detection, to yield the reporter tether in linear form;
   ligating a terminal probe to the one or more nested probes under conditions that provide for transient hybridization of the terminal probe to a third portion of the target nucleic acid sequence adjacent to the second portion of the target nucleic acid sequence to form a target identifier, wherein the terminal probe comprises a reporter tether and a probe complementary to the third portion of the target nucleic acid sequence; and
   detecting the target identifier and thereby identifying the target nucleic acid sequence in the sample.

2. The method of claim 1 wherein the probe of the capture probe comprises from 10 to 100 nucleobases.

3. The method of claim 1 wherein the capture probe is tethered to a solid support by a linker, or comprises a linker for tethering to a solid support.

4. The method of claim 1 wherein the reporter tether of the capture probe comprises a reporter code that, upon detection, parses the genetic information of the first portion of the target nucleic acid sequence to which the probe of the capture probe is complementary.

5. The method of claim 1 wherein the probes of the one or more nested probes comprise from 3 to 8 nucleobases.

6. The method of claim 1 wherein the reporter tether of the one or more nested probes comprise a reporter code that, upon detection, parses the genetic information of the second portion of the target nucleic acid sequence to which the probes of the one or more nested probes are complementary.

7. The method of claim 1 wherein the probe of the terminal probe comprises from 3 to 8 nucleobases.

8. The method of claim 1 wherein the terminal probe is tethered to a solid support by a linker, or comprises a linker for tethering to a solid support.

9. The method of claim 1 wherein the reporter tether of the terminal probe comprises a reporter code that, upon detection, parses the genetic information of the third portion of the target nucleic acid sequence to which the probe of the terminal probe is complementary.

10. The method of claim 1 wherein the target nucleic acid sequence is contacted with a plurality of capture probes, wherein the probe of each capture probe is complementary to a different target nucleic acid sequence.

11. The method of claim 10, wherein the plurality of capture probes is greater than 10, greater than 100, or greater than 1000.

12. The method of claim 1 wherein the step of ligating the terminal probe to the one or more nested probes comprises exposing the third portion of the target nucleic acid sequence to a plurality of terminal probes having probes with different combinations of nucleobases.

13. The method of claim 12 wherein the plurality of terminal probes having probes with different combinations of nucleobases is greater than 10, greater than 50, greater than 100, greater than 200, or greater than 1000.

14. The method of claim 1, further comprising at least one step of capturing, washing and concentrating the target identifier prior to detection.

15. The method of claim 1 wherein the step of detecting is accomplished by translocating the target identifier through a nanopore.

16. The method of claim 1 wherein the target identifier is amplified prior to detection.

17. The method of claim 16 wherein amplification of the target identifier is by polymerase chain reaction.

18. The method of claim 16 wherein amplification of the target identifier is by thermal cycling.

19. A method for identifying a target nucleic acid sequence in a sample, the method comprising:
   contacting the target nucleic acid sequence with a first capture probe and a second capture probe under conditions that provide for selective hybridization of the first capture probe and the second capture probe to a first portion and a second portion, respectively, of the target nucleic acid sequence, wherein the first capture probe and the second capture probe comprise a reporter tether and a probe complementary to the first portion and the second portion, respectively, of the target nucleic acid sequence;
   ligating one or more nested probes to the first capture probe and the second capture probe under conditions that provide for transient hybridization of the one or more nested probes to a portion of the target nucleic acid sequence located between the first and second portions of the target nucleic acid sequence to form a target identifier, wherein the one or more nested probes comprise probes complementary to the nucleic acid sequence located between the first and second portions of the target nucleic acid sequence, and wherein the one or more nested probes optionally comprise a reporter tether, provided that at least one of the one or more nested probes comprise a reporter tether in the form of a loop, and further comprising the step of opening the loop, prior to detection, to yield the reporter tether in linear form; and
   detecting the target identifier and thereby identifying the target nucleic acid sequence in the sample.

20. The method of claim 19 wherein the probes of the first capture probe and second capture probe comprise from 10 to 100 nucleobases.

21. The method of claim 19 wherein the first capture probe and second capture probe are tethered to a solid support by a linker, or comprises a linker for tethering to a solid support.

22. The method of claim 19 wherein the reporter tether of the first capture probe and second capture probe comprise a reporter code that, upon detection, parses the genetic information of the first portion and the second portion, respectively, of the target nucleic acid sequence to which the probe of the first capture probe and probe of the second capture probe are complementary.

23. The method of claim 19 wherein the probes of the one or more nested probes comprise from 3 to 8 nucleobases.

24. The method of claim 19 wherein the reporter tether of the one or more nested probes comprise a reporter code that, upon detection, parses the genetic information of the portion of the target nucleic acid sequence located between the first and second portions of the target nucleic acid sequence to which the probes of the one or more nested probes are complementary.

25. The method of claim 19 wherein the target nucleic acid sequence is contacted with a plurality of the first and second capture probes, wherein the probe of each of the plurality of first and second capture probe is complementary to a different target nucleic acid sequence.

26. The method of claim 25, wherein the plurality of the first and second capture probes is greater than 10, greater than 100, or greater than 1000.

27. The method of claim 19, further comprising at least one step of capturing, washing and concentrating the target identifier prior to detection.

28. The method of claim 19 wherein the step of detecting is accomplished by translocating the target identifier through a nanopore.

29. The method of claim 19 wherein the target identifier is amplified prior to detection.

30. The method of claim 29 wherein amplification of the target identifier is by polymerase chain reaction.

31. The method of claim 29 wherein amplification of the target identifier is by thermal cycling.

* * * * *